US012807708B2

(12) United States Patent
Hao et al.

(10) Patent No.: US 12,807,708 B2
(45) **Date of Patent: *Nov. 24, 2026**

(54) ANTI-CD22 ANTIBODY MOLECULE OR ANTIGEN-BINDING FRAGMENT AND USE THEREOF

(71) Applicant: KUNMING SINOWAY NATURAL PHARMACEUTICALS CO., LTD., Kunming City (CN)

(72) Inventors: Zhenping Hao, Kunming City (CN); Jianwei Zhu, Shanghai (CN); Li Xu, Kunming City (CN); Yueqing Xie, Frederick, MD (US); Hua Jiang, Frederick, MD (US); Haiqiu Huang, Frederick, MD (US)

(73) Assignee: KUNMING SINOWAY NATURAL PHARMACEUTICALS CO., LTD., Kunming City (CN)

( * ) Notice: Subject to any disclaimer, the term of this patent is extended or adjusted under 35 U.S.C. 154(b) by 654 days.

This patent is subject to a terminal disclaimer.

(21) Appl. No.: 18/246,838

(22) PCT Filed: Sep. 29, 2021

(86) PCT No.: PCT/CN2021/121826

§ 371 (c)(1),
(2) Date: Mar. 27, 2023

(87) PCT Pub. No.: WO2022/068899

PCT Pub. Date: Apr. 7, 2022

(65) Prior Publication Data

US 2023/0365679 A1 Nov. 16, 2023

(30) Foreign Application Priority Data

Sep. 29, 2020 (CN) ......................... 202011048723.0

(51) Int. Cl.

*C07K 16/28* (2006.01)
*A61K 47/68* (2017.01)
*A61P 35/02* (2006.01)

(52) U.S. Cl.

CPC ...... *C07K 16/2803* (2013.01); *A61K 47/6829* (2017.08); *A61K 47/6867* (2017.08); *A61P 35/02* (2018.01); *C07K 2317/24* (2013.01); *C07K 2317/33* (2013.01); *C07K 2317/732* (2013.01); *C07K 2317/77* (2013.01); *C07K 2317/92* (2013.01)

(58) Field of Classification Search

CPC ............ C07K 16/2803; C07K 2317/24; C07K 2319/55; C07K 1/113; A61K 2039/505; A61K 47/6849; A61P 35/00

See application file for complete search history.

(56) References Cited

U.S. PATENT DOCUMENTS

2005/0118182 A1 6/2005 Pastan et al.
2007/0189962 A1 * 8/2007 Pastan ................ C07K 16/2803 424/1.49
2012/0177567 A1 7/2012 Wayne et al.
2013/0142787 A1 6/2013 Chang et al.

FOREIGN PATENT DOCUMENTS

CN 106029098 A 10/2016
CN 107312098 A 11/2017
WO WO 2015/130416 A1 9/2015

OTHER PUBLICATIONS

Paul, WE, "Fundamental Immunology: Third Edition", 1993, Raven Press, 292-295. (Year: 1993).*
Bendig, MM, "Humanization of Rodent Monoclonal Antibodies by CDR Grafting", 1995, Methods: A Companion to Methods in Enzymology, 8, 83-93. (Year: 1995).*
Rudikoff, S. et al. "Single amino acid substitution altering antigen-binding specificity", 1982, Proceedings of the National Academy of Sciences USA, 79, 1979-1983. (Year: 1982).*
Baxevanis, CN, "Antibody-based cancer therapy", 2008, Expert Opin. Drug Discov., 3(4), 441-452. (Year: 2008).*
Wall, RJ, "Transgenic Livestock: Progress and Prospects for the Future", 1996, Theriogenology, 45, 57-68. (Year: 1996).*
Houdebine, LM, "Production of pharmaceutical proteins by transgenic animals", 2009, Comparative Immunology, Microbiology, and Infectious Diseases, 32, 107-121. (Year: 2009).*
Kappel, CA et. al. "Regulating gene expression in transgenic animals", 1992, Current Opinion in Biotechnology, 3, 548-553. (Year: 1992).*
Houdebine, LM, "Production of pharmaceutical proteins from transgenic animals", 1994, Journal of Biotechnology, 34, 269-287. (Year: 1994).*
Bang, SookHee, et al., "HA22 (R490A) is a Recombinant Immunotoxin with Increased Antitumor Activity without an Increase in Animal Toxicity," Clinical Cancer Research, vol. 11, 1545-1550, Feb. 15, 2005.
Written Opinion of International Application No. PCT/CN2021/121826, dated Dec. 27, 2021, 9 pages, and English Translation.

* cited by examiner

*Primary Examiner* — Laura B Goddard
*Assistant Examiner* — Alyssa Rae Stonebraker
(74) *Attorney, Agent, or Firm* — Lewis Roca Rothgerber Christie LLP

(57) ABSTRACT

Provided in the present invention is an isolated anti-CD22 antibody or an antigen-binding fragment thereof, and further provided is the use thereof. The antibody or the antigen binding fragment thereof shows strong identification capability for and a high affinity to CD22 recombinant protein and a CD22 positive cell line, a strong internalization capability to enter the CD22 positive cell line, and an effective growth inhibition and cell apoptosis effect on the CD22 positive cell line after fusion with bacterial exotoxin.

20 Claims, 9 Drawing Sheets

Specification includes a Sequence Listing.

A

B

C

D

E

F

G

A

B

C

A

B

C

SEQUENCE LISTING

```
<160> NUMBER OF SEQ ID NOS: 33

<210> SEQ ID NO 1
<211> LENGTH: 352
<212> TYPE: PRT
<213> ORGANISM: artificial
<220> FEATURE:
<223> OTHER INFORMATION: PE38 polypeptide sequence

<400> SEQUENCE: 1

Lys Ala Ser Gly Gly Pro Glu Gly Gly Ser Leu Ala Ala Leu Thr Ala
1               5                   10                  15

His Gln Ala Cys His Leu Pro Leu Glu Thr Phe Thr Arg His Arg Gln
            20                  25                  30

Pro Arg Gly Trp Glu Gln Leu Glu Gln Cys Gly Tyr Pro Val Gln Arg
        35                  40                  45

Leu Val Ala Leu Tyr Leu Ala Ala Arg Leu Ser Trp Asn Gln Val Asp
    50                  55                  60

Gln Val Ile Arg Asn Ala Leu Ala Ser Pro Gly Ser Gly Gly Asp Leu
65                  70                  75                  80

Gly Glu Ala Ile Arg Glu Gln Pro Glu Gln Ala Arg Leu Ala Leu Thr
                85                  90                  95

Leu Ala Ala Ala Glu Ser Glu Arg Phe Val Arg Gln Gly Thr Gly Asn
            100                 105                 110

Asp Glu Ala Gly Ala Ala Asn Gly Pro Ala Asp Ser Gly Asp Ala Leu
        115                 120                 125

Leu Glu Arg Asn Tyr Pro Thr Gly Ala Glu Phe Leu Gly Asp Gly Gly
    130                 135                 140

Asp Val Ser Phe Ser Thr Arg Gly Thr Gln Asn Trp Thr Val Glu Arg
145                 150                 155                 160

Leu Leu Gln Ala His Arg Gln Leu Glu Glu Arg Gly Tyr Val Phe Val
                165                 170                 175
```

```
Gly Tyr His Gly Thr Phe Leu Glu Ala Ala Gln Ser Ile Val Phe Gly
            180                 185                 190

Gly Val Arg Ala Arg Ser Gln Asp Leu Asp Ala Ile Trp Arg Gly Phe
        195                 200                 205

Tyr Ile Ala Gly Asp Pro Ala Leu Ala Tyr Gly Tyr Ala Gln Asp Gln
    210                 215                 220

Glu Pro Asp Ala Arg Gly Arg Ile Arg Asn Gly Ala Leu Leu Arg Val
225                 230                 235                 240

Tyr Val Pro Arg Ser Ser Leu Pro Gly Phe Tyr Arg Thr Ser Leu Thr
                245                 250                 255

Leu Ala Ala Pro Glu Ala Ala Gly Glu Val Glu Arg Leu Ile Gly His
            260                 265                 270

Pro Leu Pro Leu Arg Leu Asp Ala Ile Thr Gly Pro Glu Glu Glu Gly
        275                 280                 285

Gly Arg Leu Glu Thr Ile Leu Gly Trp Pro Leu Ala Glu Arg Thr Val
    290                 295                 300

Val Ile Pro Ser Ala Ile Pro Thr Asp Pro Arg Asn Val Gly Gly Asp
305                 310                 315                 320

Leu Asp Pro Ser Ser Ile Pro Asp Lys Glu Gln Ala Ile Ser Ala Leu
                325                 330                 335

Pro Asp Tyr Ala Ser Gln Pro Gly Lys Pro Pro Arg Glu Asp Leu Lys
            340                 345                 350


<210> SEQ ID NO 2
<211> LENGTH: 124
<212> TYPE: PRT
<213> ORGANISM: artificial
<220> FEATURE:
<223> OTHER INFORMATION: HA22, VH polypeptide sequence

<400> SEQUENCE: 2

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Gly Thr Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Leu Val Thr Val Ser Ala
        115                 120


<210> SEQ ID NO 3
<211> LENGTH: 124
<212> TYPE: PRT
<213> ORGANISM: artificial
<220> FEATURE:
<223> OTHER INFORMATION: Version 1 VH polypeptide sequence

<400> SEQUENCE: 3

Met Glu Val Gln Leu Val Glu Ser Gly Gly Gly Leu Val Lys Pro Gly
```

```
1               5                   10                  15

Gly Ser Leu Arg Leu Ser Cys Ala Ala Ser Gly Phe Ala Phe Ser Ile
            20                  25                  30

Tyr Asp Met Ser Trp Val Arg Gln Ala Pro Gly Lys Cys Leu Glu Trp
        35                  40                  45

Val Ala Tyr Ile Ser Ser Gly Gly Gly Thr Thr Tyr Tyr Pro Asp Ser
    50                  55                  60

Val Lys Gly Arg Phe Thr Ile Ser Arg Glu Asn Ala Lys Asn Ser Leu
65                  70                  75                  80

Tyr Leu Gln Met Asn Ser Leu Lys Ser Glu Asp Thr Ala Met Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Met Val Thr Val Ser Ser
        115                 120


<210> SEQ ID NO 4
<211> LENGTH: 124
<212> TYPE: PRT
<213> ORGANISM: artificial
<220> FEATURE:
<223> OTHER INFORMATION: Version 2 VH polypeptide sequence

<400> SEQUENCE: 4

Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Gly Thr Thr Tyr Tyr Pro Asp Ser
    50                  55                  60

Val Lys Gly Arg Phe Thr Ile Ser Arg Glu Asn Ala Lys Asn Ser Leu
65                  70                  75                  80

Tyr Leu Gln Met Asn Ser Leu Lys Ser Glu Asp Thr Ala Met Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Met Val Thr Val Ser Ser
        115                 120


<210> SEQ ID NO 5
<211> LENGTH: 124
<212> TYPE: PRT
<213> ORGANISM: artificial
<220> FEATURE:
<223> OTHER INFORMATION: Version 3 VH polypeptide sequence

<400> SEQUENCE: 5

Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Ala Phe Ser Ile
            20                  25                  30

Tyr Asp Met Ser Trp Ile Arg Gln Ala Pro Gly Lys Cys Leu Glu Trp
        35                  40                  45

Val Ser Tyr Ile Ser Ser Gly Gly Gly Thr Thr Tyr Tyr Pro Gly Ser
    50                  55                  60
```

-continued

```
Val Lys Gly Arg Phe Thr Ile Ser Arg Glu Asn Ala Lys Asn Ser Leu
65                  70                  75                  80

Tyr Leu Gln Met Asn Ser Leu Arg Ala Gly Asp Thr Ala Val Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Met Val Thr Val Ser Ser
        115                 120


<210> SEQ ID NO 6
<211> LENGTH: 124
<212> TYPE: PRT
<213> ORGANISM: artificial
<220> FEATURE:
<223> OTHER INFORMATION: Version 4 VH polypeptide sequence

<400> SEQUENCE: 6

Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Ala Phe Ser Ile
            20                  25                  30

Tyr Asp Met Ser Trp Ile Arg Gln Ala Pro Gly Lys Cys Leu Glu Trp
        35                  40                  45

Val Ala Tyr Ile Ser Ser Gly Gly Gly Thr Thr Tyr Tyr Pro Gly Ser
    50                  55                  60

Val Lys Gly Arg Phe Thr Ile Ser Arg Glu Asn Ala Lys Asn Ser Leu
65                  70                  75                  80

Tyr Leu Gln Met Asn Ser Leu Arg Ala Gly Asp Thr Ala Val Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Met Val Thr Val Ser Ser
        115                 120


<210> SEQ ID NO 7
<211> LENGTH: 124
<212> TYPE: PRT
<213> ORGANISM: artificial
<220> FEATURE:
<223> OTHER INFORMATION: Version 5 VH polypeptide sequence

<400> SEQUENCE: 7

Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Ala Phe Ser Ile
            20                  25                  30

Tyr Asp Met Ser Trp Ile Arg Gln Ala Pro Gly Lys Cys Leu Glu Trp
        35                  40                  45

Val Ala Tyr Ile Ser Ser Gly Gly Gly Thr Thr Tyr Tyr Pro Gly Ser
    50                  55                  60

Val Lys Gly Arg Phe Thr Ile Ser Arg Glu Asn Ala Lys Asn Ser Leu
65                  70                  75                  80

Tyr Leu Gln Met Asn Ser Leu Arg Ser Glu Asp Thr Ala Val Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Met Val Thr Val Ser Ser
        115                 120
```

<210> SEQ ID NO 8
<211> LENGTH: 476
<212> TYPE: PRT
<213> ORGANISM: artificial
<220> FEATURE:
<223> OTHER INFORMATION: HA22 VH-PE38 polypeptide sequence

<400> SEQUENCE: 8

```
Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Gly Thr Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Leu Val Thr Val Ser Ala Lys Ala Ser Gly
        115                 120                 125

Gly Pro Glu Gly Gly Ser Leu Ala Ala Leu Thr Ala His Gln Ala Cys
    130                 135                 140

His Leu Pro Leu Glu Thr Phe Thr Arg His Arg Gln Pro Arg Gly Trp
145                 150                 155                 160

Glu Gln Leu Glu Gln Cys Gly Tyr Pro Val Gln Arg Leu Val Ala Leu
                165                 170                 175

Tyr Leu Ala Ala Arg Leu Ser Trp Asn Gln Val Asp Gln Val Ile Arg
            180                 185                 190

Asn Ala Leu Ala Ser Pro Gly Ser Gly Gly Asp Leu Gly Glu Ala Ile
        195                 200                 205

Arg Glu Gln Pro Glu Gln Ala Arg Leu Ala Leu Thr Leu Ala Ala Ala
    210                 215                 220

Glu Ser Glu Arg Phe Val Arg Gln Gly Thr Gly Asn Asp Glu Ala Gly
225                 230                 235                 240

Ala Ala Asn Gly Pro Ala Asp Ser Gly Asp Ala Leu Leu Glu Arg Asn
                245                 250                 255

Tyr Pro Thr Gly Ala Glu Phe Leu Gly Asp Gly Gly Asp Val Ser Phe
            260                 265                 270

Ser Thr Arg Gly Thr Gln Asn Trp Thr Val Glu Arg Leu Leu Gln Ala
        275                 280                 285

His Arg Gln Leu Glu Glu Arg Gly Tyr Val Phe Val Gly Tyr His Gly
    290                 295                 300

Thr Phe Leu Glu Ala Ala Gln Ser Ile Val Phe Gly Gly Val Arg Ala
305                 310                 315                 320

Arg Ser Gln Asp Leu Asp Ala Ile Trp Arg Gly Phe Tyr Ile Ala Gly
                325                 330                 335

Asp Pro Ala Leu Ala Tyr Gly Tyr Ala Gln Asp Gln Glu Pro Asp Ala
            340                 345                 350

Arg Gly Arg Ile Arg Asn Gly Ala Leu Leu Arg Val Tyr Val Pro Arg
        355                 360                 365
```

Ser Ser Leu Pro Gly Phe Tyr Arg Thr Ser Leu Thr Leu Ala Ala Pro
370 375 380

Glu Ala Ala Gly Glu Val Glu Arg Leu Ile Gly His Pro Leu Pro Leu
385 390 395 400

Arg Leu Asp Ala Ile Thr Gly Pro Glu Glu Glu Gly Gly Arg Leu Glu
405 410 415

Thr Ile Leu Gly Trp Pro Leu Ala Glu Arg Thr Val Val Ile Pro Ser
420 425 430

Ala Ile Pro Thr Asp Pro Arg Asn Val Gly Gly Asp Leu Asp Pro Ser
435 440 445

Ser Ile Pro Asp Lys Glu Gln Ala Ile Ser Ala Leu Pro Asp Tyr Ala
450 455 460

Ser Gln Pro Gly Lys Pro Pro Arg Glu Asp Leu Lys
465 470 475

<210> SEQ ID NO 9
<211> LENGTH: 476
<212> TYPE: PRT
<213> ORGANISM: artificial
<220> FEATURE:
<223> OTHER INFORMATION: Version 1 VH-PE38 polypeptide sequence

<400> SEQUENCE: 9

Met Glu Val Gln Leu Val Glu Ser Gly Gly Gly Leu Val Lys Pro Gly
1 5 10 15

Gly Ser Leu Arg Leu Ser Cys Ala Ala Ser Gly Phe Ala Phe Ser Ile
20 25 30

Tyr Asp Met Ser Trp Val Arg Gln Ala Pro Gly Lys Cys Leu Glu Trp
35 40 45

Val Ala Tyr Ile Ser Ser Gly Gly Gly Thr Thr Tyr Tyr Pro Asp Ser
50 55 60

Val Lys Gly Arg Phe Thr Ile Ser Arg Glu Asn Ala Lys Asn Ser Leu
65 70 75 80

Tyr Leu Gln Met Asn Ser Leu Lys Ser Glu Asp Thr Ala Met Tyr Tyr
85 90 95

Cys Ala Arg His Ser Gly Tyr Gly Thr His Trp Gly Val Leu Phe Ala
100 105 110

Tyr Trp Gly Gln Gly Thr Met Val Thr Val Ser Ser Lys Ala Ser Gly
115 120 125

Gly Pro Glu Gly Gly Ser Leu Ala Ala Leu Thr Ala His Gln Ala Cys
130 135 140

His Leu Pro Leu Glu Thr Phe Thr Arg His Arg Gln Pro Arg Gly Trp
145 150 155 160

Glu Gln Leu Glu Gln Cys Gly Tyr Pro Val Gln Arg Leu Val Ala Leu
165 170 175

Tyr Leu Ala Ala Arg Leu Ser Trp Asn Gln Val Asp Gln Val Ile Arg
180 185 190

Asn Ala Leu Ala Ser Pro Gly Ser Gly Gly Asp Leu Gly Glu Ala Ile
195 200 205

Arg Glu Gln Pro Glu Gln Ala Arg Leu Ala Leu Thr Leu Ala Ala Ala
210 215 220

Glu Ser Glu Arg Phe Val Arg Gln Gly Thr Gly Asn Asp Glu Ala Gly
225 230 235 240

Ala Ala Asn Gly Pro Ala Asp Ser Gly Asp Ala Leu Leu Glu Arg Asn
245 250 255

```
Tyr Pro Thr Gly Ala Glu Phe Leu Gly Asp Gly Gly Asp Val Ser Phe
            260                 265                 270

Ser Thr Arg Gly Thr Gln Asn Trp Thr Val Glu Arg Leu Leu Gln Ala
        275                 280                 285

His Arg Gln Leu Glu Glu Arg Gly Tyr Val Phe Val Gly Tyr His Gly
    290                 295                 300

Thr Phe Leu Glu Ala Ala Gln Ser Ile Val Phe Gly Gly Val Arg Ala
305                 310                 315                 320

Arg Ser Gln Asp Leu Asp Ala Ile Trp Arg Gly Phe Tyr Ile Ala Gly
                325                 330                 335

Asp Pro Ala Leu Ala Tyr Gly Tyr Ala Gln Asp Gln Glu Pro Asp Ala
            340                 345                 350

Arg Gly Arg Ile Arg Asn Gly Ala Leu Leu Arg Val Tyr Val Pro Arg
        355                 360                 365

Ser Ser Leu Pro Gly Phe Tyr Arg Thr Ser Leu Thr Leu Ala Ala Pro
    370                 375                 380

Glu Ala Ala Gly Glu Val Glu Arg Leu Ile Gly His Pro Leu Pro Leu
385                 390                 395                 400

Arg Leu Asp Ala Ile Thr Gly Pro Glu Glu Glu Gly Gly Arg Leu Glu
                405                 410                 415

Thr Ile Leu Gly Trp Pro Leu Ala Glu Arg Thr Val Val Ile Pro Ser
            420                 425                 430

Ala Ile Pro Thr Asp Pro Arg Asn Val Gly Gly Asp Leu Asp Pro Ser
        435                 440                 445

Ser Ile Pro Asp Lys Glu Gln Ala Ile Ser Ala Leu Pro Asp Tyr Ala
    450                 455                 460

Ser Gln Pro Gly Lys Pro Pro Arg Glu Asp Leu Lys
465                 470                 475


<210> SEQ ID NO 10
<211> LENGTH: 476
<212> TYPE: PRT
<213> ORGANISM: artificial
<220> FEATURE:
<223> OTHER INFORMATION: Version 2 VH-PE38 polypeptide sequence

<400> SEQUENCE: 10

Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Gly Thr Thr Tyr Tyr Pro Asp Ser
    50                  55                  60

Val Lys Gly Arg Phe Thr Ile Ser Arg Glu Asn Ala Lys Asn Ser Leu
65                  70                  75                  80

Tyr Leu Gln Met Asn Ser Leu Lys Ser Glu Asp Thr Ala Met Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Met Val Thr Val Ser Ser Lys Ala Ser Gly
        115                 120                 125

Gly Pro Glu Gly Gly Ser Leu Ala Ala Leu Thr Ala His Gln Ala Cys
    130                 135                 140
```

```
His Leu Pro Leu Glu Thr Phe Thr Arg His Arg Gln Pro Arg Gly Trp
145                 150                 155                 160

Glu Gln Leu Glu Gln Cys Gly Tyr Pro Val Gln Arg Leu Val Ala Leu
                165                 170                 175

Tyr Leu Ala Ala Arg Leu Ser Trp Asn Gln Val Asp Gln Val Ile Arg
            180                 185                 190

Asn Ala Leu Ala Ser Pro Gly Ser Gly Gly Asp Leu Gly Glu Ala Ile
        195                 200                 205

Arg Glu Gln Pro Glu Gln Ala Arg Leu Ala Leu Thr Leu Ala Ala Ala
    210                 215                 220

Glu Ser Glu Arg Phe Val Arg Gln Gly Thr Gly Asn Asp Glu Ala Gly
225                 230                 235                 240

Ala Ala Asn Gly Pro Ala Asp Ser Gly Asp Ala Leu Leu Glu Arg Asn
                245                 250                 255

Tyr Pro Thr Gly Ala Glu Phe Leu Gly Asp Gly Gly Asp Val Ser Phe
            260                 265                 270

Ser Thr Arg Gly Thr Gln Asn Trp Thr Val Glu Arg Leu Leu Gln Ala
        275                 280                 285

His Arg Gln Leu Glu Glu Arg Gly Tyr Val Phe Val Gly Tyr His Gly
    290                 295                 300

Thr Phe Leu Glu Ala Ala Gln Ser Ile Val Phe Gly Gly Val Arg Ala
305                 310                 315                 320

Arg Ser Gln Asp Leu Asp Ala Ile Trp Arg Gly Phe Tyr Ile Ala Gly
                325                 330                 335

Asp Pro Ala Leu Ala Tyr Gly Tyr Ala Gln Asp Gln Glu Pro Asp Ala
            340                 345                 350

Arg Gly Arg Ile Arg Asn Gly Ala Leu Leu Arg Val Tyr Val Pro Arg
        355                 360                 365

Ser Ser Leu Pro Gly Phe Tyr Arg Thr Ser Leu Thr Leu Ala Ala Pro
    370                 375                 380

Glu Ala Ala Gly Glu Val Glu Arg Leu Ile Gly His Pro Leu Pro Leu
385                 390                 395                 400

Arg Leu Asp Ala Ile Thr Gly Pro Glu Glu Glu Gly Gly Arg Leu Glu
                405                 410                 415

Thr Ile Leu Gly Trp Pro Leu Ala Glu Arg Thr Val Val Ile Pro Ser
            420                 425                 430

Ala Ile Pro Thr Asp Pro Arg Asn Val Gly Gly Asp Leu Asp Pro Ser
        435                 440                 445

Ser Ile Pro Asp Lys Glu Gln Ala Ile Ser Ala Leu Pro Asp Tyr Ala
    450                 455                 460

Ser Gln Pro Gly Lys Pro Pro Arg Glu Asp Leu Lys
465                 470                 475
```

<210> SEQ ID NO 11
<211> LENGTH: 476
<212> TYPE: PRT
<213> ORGANISM: artificial
<220> FEATURE:
<223> OTHER INFORMATION: Version 3 VH-PE38 polypeptide sequence

<400> SEQUENCE: 11

```
Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Ala Phe Ser Ile
            20                  25                  30
```

-continued

```
Tyr Asp Met Ser Trp Ile Arg Gln Ala Pro Gly Lys Cys Leu Glu Trp
        35                  40                  45

Val Ser Tyr Ile Ser Ser Gly Gly Gly Thr Thr Tyr Tyr Pro Gly Ser
    50                  55                  60

Val Lys Gly Arg Phe Thr Ile Ser Arg Glu Asn Ala Lys Asn Ser Leu
65                  70                  75                  80

Tyr Leu Gln Met Asn Ser Leu Arg Ala Gly Asp Thr Ala Val Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Met Val Thr Val Ser Ser Lys Ala Ser Gly
        115                 120                 125

Gly Pro Glu Gly Gly Ser Leu Ala Ala Leu Thr Ala His Gln Ala Cys
    130                 135                 140

His Leu Pro Leu Glu Thr Phe Thr Arg His Arg Gln Pro Arg Gly Trp
145                 150                 155                 160

Glu Gln Leu Glu Gln Cys Gly Tyr Pro Val Gln Arg Leu Val Ala Leu
                165                 170                 175

Tyr Leu Ala Ala Arg Leu Ser Trp Asn Gln Val Asp Gln Val Ile Arg
            180                 185                 190

Asn Ala Leu Ala Ser Pro Gly Ser Gly Gly Asp Leu Gly Glu Ala Ile
        195                 200                 205

Arg Glu Gln Pro Glu Gln Ala Arg Leu Ala Leu Thr Leu Ala Ala Ala
    210                 215                 220

Glu Ser Glu Arg Phe Val Arg Gln Gly Thr Gly Asn Asp Glu Ala Gly
225                 230                 235                 240

Ala Ala Asn Gly Pro Ala Asp Ser Gly Asp Ala Leu Leu Glu Arg Asn
                245                 250                 255

Tyr Pro Thr Gly Ala Glu Phe Leu Gly Asp Gly Gly Asp Val Ser Phe
            260                 265                 270

Ser Thr Arg Gly Thr Gln Asn Trp Thr Val Glu Arg Leu Leu Gln Ala
        275                 280                 285

His Arg Gln Leu Glu Glu Arg Gly Tyr Val Phe Val Gly Tyr His Gly
    290                 295                 300

Thr Phe Leu Glu Ala Ala Gln Ser Ile Val Phe Gly Gly Val Arg Ala
305                 310                 315                 320

Arg Ser Gln Asp Leu Asp Ala Ile Trp Arg Gly Phe Tyr Ile Ala Gly
                325                 330                 335

Asp Pro Ala Leu Ala Tyr Gly Tyr Ala Gln Asp Gln Glu Pro Asp Ala
            340                 345                 350

Arg Gly Arg Ile Arg Asn Gly Ala Leu Leu Arg Val Tyr Val Pro Arg
        355                 360                 365

Ser Ser Leu Pro Gly Phe Tyr Arg Thr Ser Leu Thr Leu Ala Ala Pro
    370                 375                 380

Glu Ala Ala Gly Glu Val Glu Arg Leu Ile Gly His Pro Leu Pro Leu
385                 390                 395                 400

Arg Leu Asp Ala Ile Thr Gly Pro Glu Glu Glu Gly Gly Arg Leu Glu
                405                 410                 415

Thr Ile Leu Gly Trp Pro Leu Ala Glu Arg Thr Val Val Ile Pro Ser
            420                 425                 430

Ala Ile Pro Thr Asp Pro Arg Asn Val Gly Gly Asp Leu Asp Pro Ser
        435                 440                 445
```

```
Ser Ile Pro Asp Lys Glu Gln Ala Ile Ser Ala Leu Pro Asp Tyr Ala
    450                 455                 460

Ser Gln Pro Gly Lys Pro Pro Arg Glu Asp Leu Lys
465                 470                 475


<210> SEQ ID NO 12
<211> LENGTH: 476
<212> TYPE: PRT
<213> ORGANISM: artificial
<220> FEATURE:
<223> OTHER INFORMATION: Version 4 VH-PE38 polypeptide sequence

<400> SEQUENCE: 12

Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Ala Phe Ser Ile
            20                  25                  30

Tyr Asp Met Ser Trp Ile Arg Gln Ala Pro Gly Lys Cys Leu Glu Trp
        35                  40                  45

Val Ala Tyr Ile Ser Ser Gly Gly Gly Thr Thr Tyr Tyr Pro Gly Ser
    50                  55                  60

Val Lys Gly Arg Phe Thr Ile Ser Arg Glu Asn Ala Lys Asn Ser Leu
65                  70                  75                  80

Tyr Leu Gln Met Asn Ser Leu Arg Ala Gly Asp Thr Ala Val Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Met Val Thr Val Ser Ser Lys Ala Ser Gly
        115                 120                 125

Gly Pro Glu Gly Gly Ser Leu Ala Ala Leu Thr Ala His Gln Ala Cys
    130                 135                 140

His Leu Pro Leu Glu Thr Phe Thr Arg His Arg Gln Pro Arg Gly Trp
145                 150                 155                 160

Glu Gln Leu Glu Gln Cys Gly Tyr Pro Val Gln Arg Leu Val Ala Leu
                165                 170                 175

Tyr Leu Ala Ala Arg Leu Ser Trp Asn Gln Val Asp Gln Val Ile Arg
            180                 185                 190

Asn Ala Leu Ala Ser Pro Gly Ser Gly Gly Asp Leu Gly Glu Ala Ile
        195                 200                 205

Arg Glu Gln Pro Glu Gln Ala Arg Leu Ala Leu Thr Leu Ala Ala Ala
    210                 215                 220

Glu Ser Glu Arg Phe Val Arg Gln Gly Thr Gly Asn Asp Glu Ala Gly
225                 230                 235                 240

Ala Ala Asn Gly Pro Ala Asp Ser Gly Asp Ala Leu Leu Glu Arg Asn
                245                 250                 255

Tyr Pro Thr Gly Ala Glu Phe Leu Gly Asp Gly Gly Asp Val Ser Phe
            260                 265                 270

Ser Thr Arg Gly Thr Gln Asn Trp Thr Val Glu Arg Leu Leu Gln Ala
        275                 280                 285

His Arg Gln Leu Glu Glu Arg Gly Tyr Val Phe Val Gly Tyr His Gly
    290                 295                 300

Thr Phe Leu Glu Ala Ala Gln Ser Ile Val Phe Gly Gly Val Arg Ala
305                 310                 315                 320

Arg Ser Gln Asp Leu Asp Ala Ile Trp Arg Gly Phe Tyr Ile Ala Gly
                325                 330                 335
```

```
Asp Pro Ala Leu Ala Tyr Gly Tyr Ala Gln Asp Gln Glu Pro Asp Ala
            340                 345                 350

Arg Gly Arg Ile Arg Asn Gly Ala Leu Leu Arg Val Tyr Val Pro Arg
        355                 360                 365

Ser Ser Leu Pro Gly Phe Tyr Arg Thr Ser Leu Thr Leu Ala Ala Pro
    370                 375                 380

Glu Ala Ala Gly Glu Val Glu Arg Leu Ile Gly His Pro Leu Pro Leu
385                 390                 395                 400

Arg Leu Asp Ala Ile Thr Gly Pro Glu Glu Glu Gly Gly Arg Leu Glu
                405                 410                 415

Thr Ile Leu Gly Trp Pro Leu Ala Glu Arg Thr Val Val Ile Pro Ser
            420                 425                 430

Ala Ile Pro Thr Asp Pro Arg Asn Val Gly Gly Asp Leu Asp Pro Ser
        435                 440                 445

Ser Ile Pro Asp Lys Glu Gln Ala Ile Ser Ala Leu Pro Asp Tyr Ala
    450                 455                 460

Ser Gln Pro Gly Lys Pro Pro Arg Glu Asp Leu Lys
465                 470                 475


<210> SEQ ID NO 13
<211> LENGTH: 476
<212> TYPE: PRT
<213> ORGANISM: artificial
<220> FEATURE:
<223> OTHER INFORMATION: Version 5 VH-PE38 polypeptide sequence

<400> SEQUENCE: 13

Met Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Ala Phe Ser Ile
            20                  25                  30

Tyr Asp Met Ser Trp Ile Arg Gln Ala Pro Gly Lys Cys Leu Glu Trp
        35                  40                  45

Val Ala Tyr Ile Ser Ser Gly Gly Gly Thr Thr Tyr Tyr Pro Gly Ser
    50                  55                  60

Val Lys Gly Arg Phe Thr Ile Ser Arg Glu Asn Ala Lys Asn Ser Leu
65                  70                  75                  80

Tyr Leu Gln Met Asn Ser Leu Arg Ser Glu Asp Thr Ala Val Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Met Val Thr Val Ser Ser Lys Ala Ser Gly
        115                 120                 125

Gly Pro Glu Gly Gly Ser Leu Ala Ala Leu Thr Ala His Gln Ala Cys
    130                 135                 140

His Leu Pro Leu Glu Thr Phe Thr Arg His Arg Gln Pro Arg Gly Trp
145                 150                 155                 160

Glu Gln Leu Glu Gln Cys Gly Tyr Pro Val Gln Arg Leu Val Ala Leu
                165                 170                 175

Tyr Leu Ala Ala Arg Leu Ser Trp Asn Gln Val Asp Gln Val Ile Arg
            180                 185                 190

Asn Ala Leu Ala Ser Pro Gly Ser Gly Gly Asp Leu Gly Glu Ala Ile
        195                 200                 205

Arg Glu Gln Pro Glu Gln Ala Arg Leu Ala Leu Thr Leu Ala Ala Ala
    210                 215                 220
```

```
Glu Ser Glu Arg Phe Val Arg Gln Gly Thr Gly Asn Asp Glu Ala Gly
225                 230                 235                 240

Ala Ala Asn Gly Pro Ala Asp Ser Gly Asp Ala Leu Leu Glu Arg Asn
                245                 250                 255

Tyr Pro Thr Gly Ala Glu Phe Leu Gly Asp Gly Gly Asp Val Ser Phe
            260                 265                 270

Ser Thr Arg Gly Thr Gln Asn Trp Thr Val Glu Arg Leu Leu Gln Ala
        275                 280                 285

His Arg Gln Leu Glu Glu Arg Gly Tyr Val Phe Val Gly Tyr His Gly
    290                 295                 300

Thr Phe Leu Glu Ala Ala Gln Ser Ile Val Phe Gly Gly Val Arg Ala
305                 310                 315                 320

Arg Ser Gln Asp Leu Asp Ala Ile Trp Arg Gly Phe Tyr Ile Ala Gly
                325                 330                 335

Asp Pro Ala Leu Ala Tyr Gly Tyr Ala Gln Asp Gln Glu Pro Asp Ala
            340                 345                 350

Arg Gly Arg Ile Arg Asn Gly Ala Leu Leu Arg Val Tyr Val Pro Arg
        355                 360                 365

Ser Ser Leu Pro Gly Phe Tyr Arg Thr Ser Leu Thr Leu Ala Ala Pro
    370                 375                 380

Glu Ala Ala Gly Glu Val Glu Arg Leu Ile Gly His Pro Leu Pro Leu
385                 390                 395                 400

Arg Leu Asp Ala Ile Thr Gly Pro Glu Glu Glu Gly Gly Arg Leu Glu
                405                 410                 415

Thr Ile Leu Gly Trp Pro Leu Ala Glu Arg Thr Val Val Ile Pro Ser
            420                 425                 430

Ala Ile Pro Thr Asp Pro Arg Asn Val Gly Gly Asp Leu Asp Pro Ser
        435                 440                 445

Ser Ile Pro Asp Lys Glu Gln Ala Ile Ser Ala Leu Pro Asp Tyr Ala
    450                 455                 460

Ser Gln Pro Gly Lys Pro Pro Arg Glu Asp Leu Lys
465                 470                 475


<210> SEQ ID NO 14
<211> LENGTH: 108
<212> TYPE: PRT
<213> ORGANISM: artificial
<220> FEATURE:
<223> OTHER INFORMATION: HA22, VL polypeptide sequence

<400> SEQUENCE: 14

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Ser Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Ile Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Phe Ala Thr Tyr Phe Cys Gln Gln Gly Asn Thr Leu Pro
                85                  90                  95

Trp Thr Phe Gly Cys Gly Thr Lys Leu Glu Ile Lys
            100                 105
```

<210> SEQ ID NO 15
<211> LENGTH: 108
<212> TYPE: PRT
<213> ORGANISM: artificial
<220> FEATURE:
<223> OTHER INFORMATION: Version 1 VL polypeptide sequence

<400> SEQUENCE: 15

```
Met Asp Ile Gln Met Thr Gln Ser Pro Ser Thr Leu Ser Ala Ser Val
1               5                   10                  15

Gly Asp Arg Val Thr Ile Thr Cys Arg Ala Ser Gln Asp Ile Ser Asn
            20                  25                  30

Tyr Leu Asn Trp Tyr Gln Gln Arg Pro Gly Gln Ser Val Lys Leu Leu
        35                  40                  45

Ile Tyr Tyr Thr Ser Ile Leu His Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Phe Cys Gln Gln Gly Asn Thr Leu Pro
                85                  90                  95

Trp Thr Phe Gly Cys Gly Thr Lys Val Glu Ile Lys
            100                 105
```

<210> SEQ ID NO 16
<211> LENGTH: 108
<212> TYPE: PRT
<213> ORGANISM: artificial
<220> FEATURE:
<223> OTHER INFORMATION: Version 2 VL polypeptide sequence

<400> SEQUENCE: 16

```
Met Asp Ile Gln Met Thr Gln Ser Thr Ser Thr Leu Ser Ala Ser Val
1               5                   10                  15

Gly Asp Arg Val Thr Ile Thr Cys Arg Ala Ser Gln Asp Ile Ser Asn
            20                  25                  30

Tyr Leu Asn Trp Tyr Gln Gln Arg Pro Asp Gly Ser Val Lys Leu Leu
        35                  40                  45

Ile Tyr Tyr Thr Ser Ile Leu His Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Asp Glu Asp Phe Ala Thr Tyr Phe Cys Gln Gln Gly Asn Thr Leu Pro
                85                  90                  95

Trp Thr Phe Gly Cys Gly Thr Lys Val Glu Ile Lys
            100                 105
```

<210> SEQ ID NO 17
<211> LENGTH: 108
<212> TYPE: PRT
<213> ORGANISM: artificial
<220> FEATURE:
<223> OTHER INFORMATION: Version 3 VL polypeptide sequence

<400> SEQUENCE: 17

```
Met Asp Ile Gln Met Thr Gln Ser Pro Ser Thr Leu Ser Ala Ser Val
1               5                   10                  15

Gly Asp Arg Val Thr Ile Thr Cys Arg Ala Ser Gln Asp Ile Ser Asn
            20                  25                  30

Tyr Leu Asn Trp Phe Gln Gln Arg Pro Gly Gln Ser Pro Arg Arg Leu
```

```
        35                  40                  45

Ile Tyr Tyr Thr Ser Ile Leu His Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Asn Thr Leu Pro
                85                  90                  95

Trp Thr Phe Gly Cys Gly Thr Lys Val Glu Ile Lys
            100                 105


<210> SEQ ID NO 18
<211> LENGTH: 108
<212> TYPE: PRT
<213> ORGANISM: artificial
<220> FEATURE:
<223> OTHER INFORMATION: Version 4 VL polypeptide sequence

<400> SEQUENCE: 18

Met Asp Ile Gln Met Thr Gln Ser Pro Ser Thr Leu Ser Ala Ser Val
1               5                   10                  15

Gly Asp Arg Val Thr Ile Thr Cys Arg Ala Ser Gln Asp Ile Ser Asn
            20                  25                  30

Tyr Leu Asn Trp Phe Gln Gln Arg Pro Gly Gln Ser Pro Arg Leu Leu
        35                  40                  45

Ile Tyr Tyr Thr Ser Ile Leu His Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Asn Thr Leu Pro
                85                  90                  95

Trp Thr Phe Gly Cys Gly Thr Lys Val Glu Ile Lys
            100                 105


<210> SEQ ID NO 19
<211> LENGTH: 1428
<212> TYPE: DNA
<213> ORGANISM: artificial
<220> FEATURE:
<223> OTHER INFORMATION: Version 1 VH-PE38 DNA sequence

<400> SEQUENCE: 19

atggaagtgc agctggtgga atccggcgga ggcctggtca agcccggcgg ctctctgaga      60

ctgtcctgcg ctgcttctgg cttcgccttc tccatctacg acatgtcctg ggtcagacag     120

gcccctggca agtgcctgga atgggtggcc tacatctcct ctggcggagg caccacctac     180

taccctgact ccgtgaaggg cagattcacc atctctagag agaacgccaa gaacagcctg     240

tacctgcaga tgaactccct gaagtccgag gacaccgcca tgtactactg cgccagacac     300

tccggctacg gcacacactg gggcgtgctg ttcgcttact ggggccaggg caccatggtg     360

accgtgtcct ccaaagcgtc aggcggtccg gaaggcggtt cgctggcagc tctgaccgca     420

catcaggcat gccacctgcc gctggaaacc tttacccgcc atcgtcaacc gcgcggctgg     480

gaacagctgg aacaatgtgg ttatccggtg cagcgcctgg ttgccctgta cctggccgca     540

cgtctgagct ggaaccaggt tgatcaagtc attcgtaatg cgctggcatc accgggctcg     600

ggcggtgacc tgggtgaagc aatccgcgaa cagccggaac aagcgcgcct ggccctgacc     660

ctggcagctg cggaatccga acgctttgtg cgtcagggca ccggtaatga tgaagccggt     720
```

gcagcaaatg gtccggctga ttcaggtgac gcgctgctgg aacgcaacta tccgacgggc 780
gccgaatttc tgggtgatgg cggtgacgtg agtttctcca cccgcggcac gcagaattgg 840
accgttgaac gtctgctgca ggcgcatcgc caactggaag aacgtggtta tgtttttgtc 900
ggctatcatg gcacctttct ggaagctgcg cagtcgattg tctttggcgg tgtgcgtgca 960
cgcagccagg atctggatgc aatttggcgc ggcttctaca tcgcaggtga tccggctctg 1020
gcgtatggct acgctcagga tcaagaaccg gatgcgcgtg gccgcatccg taatggtgcc 1080
ctgctgcgtg tgtatgttcc gcgttcatcg ctgccgggtt tttaccgtac ctctctgacc 1140
ctggcggcac cggaagctgc cggcgaagtg gaacgcctga ttggtcaccc gctgccgctg 1200
cgtctggatg caatcaccgg tccggaagaa gaaggcggcc gtctggaaac gattctgggt 1260
tggccgctgg ccgaacgtac cgtggttatt ccgagcgcaa tcccgacgga cccgcgcaat 1320
gttggcggtg atctggaccc gagctctatt ccggataaag aacaggccat ctccgcactg 1380
ccggactatg cgtcacaacc gggcaaaccg ccgcgtgaag acctgaaa 1428

<210> SEQ ID NO 20
<211> LENGTH: 1428
<212> TYPE: DNA
<213> ORGANISM: artificial
<220> FEATURE:
<223> OTHER INFORMATION: Version 2 VH-PE38 DNA sequence

<400> SEQUENCE: 20
atggaagtgc agctggtgga atccggcgga ggcctggtca agcccggcgg ctctctgaga 60
ctgtcctgcg ctgcttctgg cttcgccttc tccatctacg acatgtcctg ggtcagacag 120
acccctgaaa agtgcctgga atgggtggcc tacatctcct ctggcggagg caccacctac 180
taccctgact ccgtgaaggg cagattcacc atctctagag agaacgccaa gaacagcctg 240
tacctgcaga tgaactccct gaagtccgag gacaccgcca tgtactactg cgccagacac 300
tccggctacg gcacacactg ggcgtgctg ttcgcttact ggggccaggg caccatggtg 360
accgtgtcct ccaaagcgtc aggcggtccg gaaggcggtt cgctggcagc tctgaccgca 420
catcaggcat gccacctgcc gctggaaacc tttacccgcc atcgtcaacc gcgcggctgg 480
gaacagctgg aacaatgtgg ttatccggtg cagcgcctgg ttgccctgta cctggccgca 540
cgtctgagct ggaaccaggt tgatcaagtc attcgtaatg cgctggcatc accgggctcg 600
ggcggtgacc tgggtgaagc aatccgcgaa cagccggaac aagcgcgcct ggccctgacc 660
ctggcagctg cggaatccga acgctttgtg cgtcagggca ccggtaatga tgaagccggt 720
gcagcaaatg gtccggctga ttcaggtgac gcgctgctgg aacgcaacta tccgacgggc 780
gccgaatttc tgggtgatgg cggtgacgtg agtttctcca cccgcggcac gcagaattgg 840
accgttgaac gtctgctgca ggcgcatcgc caactggaag aacgtggtta tgtttttgtc 900
ggctatcatg gcacctttct ggaagctgcg cagtcgattg tctttggcgg tgtgcgtgca 960
cgcagccagg atctggatgc aatttggcgc ggcttctaca tcgcaggtga tccggctctg 1020
gcgtatggct acgctcagga tcaagaaccg gatgcgcgtg gccgcatccg taatggtgcc 1080
ctgctgcgtg tgtatgttcc gcgttcatcg ctgccgggtt tttaccgtac ctctctgacc 1140
ctggcggcac cggaagctgc cggcgaagtg gaacgcctga ttggtcaccc gctgccgctg 1200
cgtctggatg caatcaccgg tccggaagaa gaaggcggcc gtctggaaac gattctgggt 1260
tggccgctgg ccgaacgtac cgtggttatt ccgagcgcaa tcccgacgga cccgcgcaat 1320
gttggcggtg atctggaccc gagctctatt ccggataaag aacaggccat ctccgcactg 1380

```
ccggactatg cgtcacaacc gggcaaaccg ccgcgtgaag acctgaaa              1428


<210> SEQ ID NO 21
<211> LENGTH: 1428
<212> TYPE: DNA
<213> ORGANISM: artificial
<220> FEATURE:
<223> OTHER INFORMATION: Version 3 VH-PE38 DNA sequence

<400> SEQUENCE: 21

atggaagtgc agctggttga aagcggtggc ggtctggtga aaccgggcgg tagcctgcgt     60

ctgagctgcg cggcgagcgg tttcgcgttt agcatctacg acatgagctg gattcgtcaa    120

gcgccgggca aatgcctgga gtgggtgagc tatatcagca gcggcggtgg caccacctac    180

tatccgggta gcgttaaggg ccgtttcacc attagccgtg aaaacgcgaa aaacagcctg    240

tacctgcaga tgaacagcct gcgtgcgggt gataccgctg tgtactattg cgcgcgtcac    300

agcggttacg gcacccactg ggcgttctg tttgcgtatt ggggtcaagg caccatggtg    360

accgttagca gcaaagcgtc aggcggtccg gaaggcggtt cgctggcagc tctgaccgca    420

catcaggcat gccacctgcc gctggaaacc tttacccgcc atcgtcaacc gcgcggctgg    480

gaacagctgg aacaatgtgg ttatccggtg cagcgcctgg ttgccctgta cctggccgca    540

cgtctgagct ggaaccaggt tgatcaagtc attcgtaatg cgctggcatc accgggctcg    600

ggcggtgacc tgggtgaagc aatccgcgaa cagccggaac aagcgcgcct ggccctgacc    660

ctggcagctg cggaatccga acgctttgtg cgtcagggca ccggtaatga tgaagccggt    720

gcagcaaatg gtccggctga ttcaggtgac gcgctgctgg aacgcaacta tccgacgggc    780

gccgaatttc tgggtgatgg cggtgacgtg agtttctcca cccgcggcac gcagaattgg    840

accgttgaac gtctgctgca ggcgcatcgc caactggaag aacgtggtta tgtttttgtc    900

ggctatcatg gcacctttct ggaagctgcg cagtcgattg tctttggcgg tgtgcgtgca    960

cgcagccagg atctggatgc aatttggcgc ggcttctaca tcgcaggtga tccggctctg   1020

gcgtatggct acgctcagga tcaagaaccg gatgcgcgtg gccgcatccg taatggtgcc   1080

ctgctgcgtg tgtatgttcc gcgttcatcg ctgccgggtt tttaccgtac ctctctgacc   1140

ctggcggcac cggaagctgc cggcgaagtg gaacgcctga ttggtcaccc gctgccgctg   1200

cgtctggatg caatcaccgg tccggaagaa gaaggcggcc gtctggaaac gattctgggt   1260

tggccgctgg ccgaacgtac cgtggttatt ccgagcgcaa tcccgacgga cccgcgcaat   1320

gttggcggtg atctggaccc gagctctatt ccggataaag aacaggccat ctccgcactg   1380

ccggactatg cgtcacaacc gggcaaaccg ccgcgtgaag acctgaaa              1428


<210> SEQ ID NO 22
<211> LENGTH: 1428
<212> TYPE: DNA
<213> ORGANISM: artificial
<220> FEATURE:
<223> OTHER INFORMATION: Version 4 VH-PE38 DNA sequence

<400> SEQUENCE: 22

atggaagtgc agctggttga aagcggtggc ggtctggtga aaccgggcgg tagcctgcgt     60

ctgagctgcg cggcgagcgg tttcgcgttt agcatctacg acatgagctg gattcgtcaa    120

gcgccgggca aatgcctgga gtgggtggcg tatatcagca gcggcggtgg caccacctac    180

tatccgggta gcgttaaggg ccgtttcacc attagccgtg aaaacgcgaa aaacagcctg    240
```

tacctgcaga tgaacagcct gcgtgcgggt gataccgctg tgtactattg cgcgcgtcac 300
agcggttacg gcacccactg ggcgttctg tttgcgtatt ggggtcaagg caccatggtg 360
accgttagca gcaaagcgtc aggcggtccg gaaggcggtt cgctggcagc tctgaccgca 420
catcaggcat gccacctgcc gctggaaacc tttacccgcc atcgtcaacc gcgcggctgg 480
gaacagctgg aacaatgtgg ttatccggtg cagcgcctgg ttgccctgta cctggccgca 540
cgtctgagct ggaaccaggt tgatcaagtc attcgtaatg cgctggcatc accgggctcg 600
ggcggtgacc tgggtgaagc aatccgcgaa cagccggaac aagcgcgcct ggccctgacc 660
ctggcagctg cggaatccga acgctttgtg cgtcagggca ccggtaatga tgaagccggt 720
gcagcaaatg gtccggctga ttcaggtgac gcgctgctgg aacgcaacta tccgacgggc 780
gccgaatttc tgggtgatgg cggtgacgtg agtttctcca cccgcggcac gcagaattgg 840
accgttgaac gtctgctgca ggcgcatcgc caactggaag aacgtggtta tgtttttgtc 900
ggctatcatg gcacctttct ggaagctgcg cagtcgattg tctttggcgg tgtgcgtgca 960
cgcagccagg atctggatgc aatttggcgc ggcttctaca tcgcaggtga tccggctctg 1020
gcgtatggct acgctcagga tcaagaaccg gatgcgcgtg gccgcatccg taatggtgcc 1080
ctgctgcgtg tgtatgttcc gcgttcatcg ctgccgggtt tttaccgtac ctctctgacc 1140
ctggcggcac cggaagctgc cggcgaagtg gaacgcctga ttggtcaccc gctgccgctg 1200
cgtctggatg caatcaccgg tccggaagaa gaaggcggcc gtctggaaac gattctgggt 1260
tggccgctgg ccgaacgtac cgtggttatt ccgagcgcaa tcccgacgga cccgcgcaat 1320
gttggcggtg atctggaccc gagctctatt ccggataaag aacaggccat ctccgcactg 1380
ccggactatg cgtcacaacc gggcaaaccg ccgcgtgaag acctgaaa 1428

<210> SEQ ID NO 23
<211> LENGTH: 1428
<212> TYPE: DNA
<213> ORGANISM: artificial
<220> FEATURE:
<223> OTHER INFORMATION: Version 5 VH-PE38 DNA sequence

<400> SEQUENCE: 23
atggaagtgc agctggttga aagcggtggc ggtctggtga aaccgggcgg tagcctgcgt 60
ctgagctgcg cggcgagcgg tttcgcgttt agcatctacg acatgagctg gattcgtcaa 120
gcgccgggca aatgcctgga gtgggtggcg tatatcagca gcggcggtgg caccacctac 180
tatccgggta gcgttaaggg ccgtttcacc attagccgtg aaaacgcgaa aaacagcctg 240
tacctgcaga tgaacagcct gcgttctgag gataccgctg tgtactattg cgcgcgtcac 300
agcggttacg gcacccactg ggcgttctg tttgcgtatt ggggtcaagg caccatggtg 360
accgttagca gcaaagcgtc aggcggtccg gaaggcggtt cgctggcagc tctgaccgca 420
catcaggcat gccacctgcc gctggaaacc tttacccgcc atcgtcaacc gcgcggctgg 480
gaacagctgg aacaatgtgg ttatccggtg cagcgcctgg ttgccctgta cctggccgca 540
cgtctgagct ggaaccaggt tgatcaagtc attcgtaatg cgctggcatc accgggctcg 600
ggcggtgacc tgggtgaagc aatccgcgaa cagccggaac aagcgcgcct ggccctgacc 660
ctggcagctg cggaatccga acgctttgtg cgtcagggca ccggtaatga tgaagccggt 720
gcagcaaatg gtccggctga ttcaggtgac gcgctgctgg aacgcaacta tccgacgggc 780
gccgaatttc tgggtgatgg cggtgacgtg agtttctcca cccgcggcac gcagaattgg 840
accgttgaac gtctgctgca ggcgcatcgc caactggaag aacgtggtta tgtttttgtc 900

```
ggctatcatg gcacctttct ggaagctgcg cagtcgattg tctttggcgg tgtgcgtgca    960

cgcagccagg atctggatgc aatttggcgc ggcttctaca tcgcaggtga tccggctctg   1020

gcgtatggct acgctcagga tcaagaaccg gatgcgcgtg gccgcatccg taatggtgcc   1080

ctgctgcgtg tgtatgttcc gcgttcatcg ctgccgggtt tttaccgtac ctctctgacc   1140

ctggcggcac cggaagctgc cggcgaagtg gaacgcctga ttggtcaccc gctgccgctg   1200

cgtctggatg caatcaccgg tccggaagaa gaaggcggcc gtctggaaac gattctgggt   1260

tggccgctgg ccgaacgtac cgtggttatt ccgagcgcaa tcccgacgga cccgcgcaat   1320

gttggcggtg atctggaccc gagctctatt ccggataaag aacaggccat ctccgcactg   1380

ccggactatg cgtcacaacc gggcaaaccg ccgcgtgaag acctgaaa                1428
```

<210> SEQ ID NO 24
<211> LENGTH: 324
<212> TYPE: DNA
<213> ORGANISM: artificial
<220> FEATURE:
<223> OTHER INFORMATION: Version 1 VL DNA sequence

<400> SEQUENCE: 24

```
atggacatcc agatgaccca gtctccttct acactgtctg cttctgtggg cgacagagtg     60

accatcacct gcagagcctc tcaggacatc tccaactacc tgaactggta ccagcagaga    120

cctggccagt ccgtgaagct gctgatctac tacacctcca tcctgcactc cggcgtgcct    180

tccagattct ccggctctgg atctggcacc gactacaccc tgaccatctc ctccctgcag    240

cctgaggact tcgccaccta cttctgccag cagggcaaca ccctgccttg gaccttcggc    300

tgcggcacca aggtggaaat caag                                           324
```

<210> SEQ ID NO 25
<211> LENGTH: 324
<212> TYPE: DNA
<213> ORGANISM: artificial
<220> FEATURE:
<223> OTHER INFORMATION: Version 2 VL DNA sequence

<400> SEQUENCE: 25

```
atggacatcc agatgaccca gtctacttct acactgtctg cttctgtggg cgacagagtg     60

accatcacct gcagagcctc tcaggacatc tccaactacc tgaactggta ccagcagaga    120

cctgatggct ccgtgaagct gctgatctac tacacctcca tcctgcactc cggcgtgcct    180

tccagattct ccggctctgg atctggcacc gactacaccc tgaccatctc ctccctgcag    240

gatgaggact tcgccaccta cttctgccag cagggcaaca ccctgccttg gaccttcggc    300

tgcggcacca aggtggaaat caag                                           324
```

<210> SEQ ID NO 26
<211> LENGTH: 324
<212> TYPE: DNA
<213> ORGANISM: artificial
<220> FEATURE:
<223> OTHER INFORMATION: Version 3 VL DNA sequence

<400> SEQUENCE: 26

```
atggacatcc agatgaccca gagcccgagc accctgagcg cgagcgtggg cgaccgtgtt     60

accatcacct gccgtgcgag ccaggatatt agcaactacc tgaactggtt tcaacaacgt    120

ccgggtcaaa gcccgcgtcg tctgatctac tataccagca ttctgcacag cggtgtgccg    180
```

agccgtttta gcggtagcgg cagcggtacc gactataccc tgaccatcag cagcctgcag 240
ccggaggatt tcgcgaccta ctattgccag cagggtaaca ccctgccgtg gacctttggc 300
tgcggtacca aggttgaaat taaa 324

<210> SEQ ID NO 27
<211> LENGTH: 324
<212> TYPE: DNA
<213> ORGANISM: artificial
<220> FEATURE:
<223> OTHER INFORMATION: Version 3 VL DNA sequence

<400> SEQUENCE: 27
atggacatcc agatgaccca gagcccgagc accctgagcg cgagcgtggg cgaccgtgtt 60
accatcacct gccgtgcgag ccaggatatt agcaactacc tgaactggtt tcaacaacgt 120
ccgggtcaaa gcccgcgtct gctgatctac tataccagca ttctgcacag cggtgtgccg 180
agccgtttta gcggtagcgg cagcggtacc gactataccc tgaccatcag cagcctgcag 240
ccggaggatt tcgcgaccta ctattgccag cagggtaaca ccctgccgtg gacctttggc 300
tgcggtacca aggttgaaat taaa 324

<210> SEQ ID NO 28
<211> LENGTH: 8
<212> TYPE: PRT
<213> ORGANISM: artificial
<220> FEATURE:
<223> OTHER INFORMATION: HA22, H-CDR1

<400> SEQUENCE: 28

Gly Phe Ala Phe Ser Ile Tyr Asp
1               5

<210> SEQ ID NO 29
<211> LENGTH: 9
<212> TYPE: PRT
<213> ORGANISM: artificial
<220> FEATURE:
<223> OTHER INFORMATION: HA22, H-CDR2

<400> SEQUENCE: 29

Ile Ser Ser Gly Gly Gly Thr Thr Tyr
1               5

<210> SEQ ID NO 30
<211> LENGTH: 17
<212> TYPE: PRT
<213> ORGANISM: artificial
<220> FEATURE:
<223> OTHER INFORMATION: HA22, H-CDR3

<400> SEQUENCE: 30

Cys Ala Arg His Ser Gly Tyr Gly Thr His Trp Gly Val Leu Phe Ala
1               5                   10                  15

Tyr

<210> SEQ ID NO 31
<211> LENGTH: 6
<212> TYPE: PRT
<213> ORGANISM: artificial
<220> FEATURE:
<223> OTHER INFORMATION: HA22, L-CDR1

<400> SEQUENCE: 31

-continued

```
Gln Asp Ile Ser Asn Tyr
1               5


<210> SEQ ID NO 32
<211> LENGTH: 8
<212> TYPE: PRT
<213> ORGANISM: artificial
<220> FEATURE:
<223> OTHER INFORMATION: HA22, L-CDR2

<400> SEQUENCE: 32

Tyr Thr Ser Ile Leu His Ser Gly
1               5


<210> SEQ ID NO 33
<211> LENGTH: 7
<212> TYPE: PRT
<213> ORGANISM: artificial
<220> FEATURE:
<223> OTHER INFORMATION: HA22, L-CDR3

<400> SEQUENCE: 33

Gln Gln Gly Asn Thr Leu Pro
1               5
```

ANTI-CD22 ANTIBODY MOLECULE OR ANTIGEN-BINDING FRAGMENT AND USE THEREOF

CROSS-REFERENCE TO RELATED APPLICATIONS

The present patent application is a U.S. National Phase Patent Application of International Application Number PCT/CN2021/121826, filed on Sep. 29, 2021, which claims the priority benefit of Chinese patent application No. CN202011048723.0 filed on Sep. 29, 2020, the entire content of each of which is hereby incorporated by reference.

SEQUENCE LISTING

The instant application contains a Sequence Listing submitted in ASCII format via EFS-web and is incorporated herein by reference in its entirety for all purposes. Said ASCII copy is named "LC21210009PEnglishtranslatioSequenceListing.txt," was last modified on Mar. 19, 2023, and is 39.2 KB in size.

TECHNICAL FIELD

The present disclosure relates to the field of biomedicine, in particular to a novel humanized anti-CD22 antibody and application thereof.

BACKGROUND OF THE INVENTION

CD22 (Siglec-2) is a sialic acid-binding immunoglobulin-like lectin (Siglec) receptor, that binds specifically to sialic acid (Sia)-containing glycans, facilitating cell adhesion and/or cell signaling. CD22 expression is restricted to B cells and plays a critical role in establishing a baseline level of B-cell inhibition, and thus is a critical determinant of homeostasis in humoral immunity. CD22 is expressed in neoplastic cells in various B-cell malignancies, including B-lymphocytic leukemias/lymphomas and mature B-cell leukemias/lymphomas. The expression of CD22 can be particularly strong in hairy cell leukemia (HCL) and prolymphocytic leukemia.

Studies have shown that anti-CD22 antibodies can be used in the treatment of autoimmune diseases and B cell tumors. In addition, anti-CD22 antibodies are often developed for conjugation to other drugs, such as cytotoxic agents, enabling the targeted delivery of the drugs to target cells by means of their targeting properties.

Accordingly, there is a need in the art for a novel anti-CD22 antibody or fragment thereof that has a high affinity for CD22 and can be used in the treatment of CD22-related diseases, either alone or when conjugated to other drugs or molecules.

SUMMARY OF THE INVENTION

In order to solve the above technical problem, the present disclosure provides an isolated monoclonal antibody, which is a humanized anti-CD22 antibody that binds to CD22 and exhibits strong recognition ability and high affinity for recombinant CD22 protein and CD22-positive cells, strong internalization ability into CD22-positive cells, and potent growth inhibition and apoptosis induction effects on CD22-positive cells after fused with a bacterial exotoxin. Based on the isolated monoclonal antibody, the present disclosure provides various antibody formats comprising key domains of the antibody and corresponding uses thereof.

Technical solutions of the invention are as follows.

In one aspect, the present disclosure provides an isolated anti-CD22 antibody or antigen binding fragment thereof. As used herein, the "antigen binding fragment" of the antibody encompasses various functional fragments of the antibody that retain the binding ability of the antibody to CD22 and corresponding biological activities of the antibody.

With respect to sequence structure, the present disclosure provides an isolated anti-CD22 antibody or antigen-binding fragment thereof, comprising a heavy chain variable region (VH) and a light chain variable region (VL), wherein the heavy chain variable region (VH) and light chain variable region (VL) comprise respectively:

(1) H-CDR1 having an amino acid sequence as shown in SEQ ID NO. 19 (IYDMS), H-CDR2 having an amino acid sequence as shown in SEQ ID NO. 25 (YISSGGGTTYYPDSVKG), and H-CDR3 having an amino acid sequence as shown in SEQ ID NO. 21 (HSGYGTHWGVLFAY); and, L-CDR1 having an amino acid sequence as shown in SEQ ID NO. 22 (RASQDISNYLN), L-CDR2 having an amino acid sequence as shown in SEQ ID NO. 23 (YTSILHS), and L-CDR3 having an amino acid sequence as shown in SEQ ID NO. 24 (QQGNTLPWT); or (2) H-CDR1 having an amino acid sequence as shown in SEQ ID NO. 19 (IYDMS), H-CDR2 having an amino acid sequence as shown in SEQ ID NO. 26 (YISSGGGTTYYPGSVKG), and H-CDR3 having an amino acid sequence as shown in SEQ ID NO. 21 (HSGYGTHWGVLFAY); and, L-CDR1 having an amino acid sequence as shown in SEQ ID NO. 22 (RASQDISNYLN), L-CDR2 having an amino acid sequence as shown in SEQ ID NO. 23 (YTSILHS), and L-CDR3 having an amino acid sequence as shown in SEQ ID NO. 24 (QQGNTLPWT).

The anti-CD22 antibody or antigen-binding fragment thereof provided by the present disclosure is capable of binding to antigen CD22, particularly human CD22, with high affinity.

Preferably, in the anti-CD22 antibody or antigen binding fragment thereof provided by the present disclosure, the heavy chain variable region may comprise an amino acid sequence as shown in SEQ ID NO: 4, SEQ ID NO: 3, SEQ ID NO: 6, or SEQ ID NO: 5, or an amino acid sequence having at least 75% identity to the amino acid sequence as shown in SEQ ID NO: 4, SEQ ID NO: 3, SEQ ID NO: 6, or SEQ ID NO: 5; and/or, the light chain variable region comprises an amino acid sequence as shown in SEQ ID NO: 2, SEQ ID NO: 7, or SEQ ID NO: 8, or an amino acid sequence having at least 75% of identity to the amino acid sequence as shown in SEQ ID NO: 2, SEQ ID NO: 7, or SEQ ID NO: 8.

The "at least 75% identity" as used in the context of the present disclosure with respect to sequence is any percent identity no less than 75%, such as at least 80%, preferably at least 85%, more preferably at least 90%, further preferably at least 91%, 92%, 93%, 94%, 95%, 96%, 97%, 98% or even 99% identity.

Further preferably, in the antibody or antigen binding fragment thereof provided by the present disclosure, the heavy chain variable region and the light chain variable region comprise respectively:

(1) an amino acid sequence as shown in SEQ ID NO: 4 or an amino acid sequence having at least 75% identity to the amino acid sequence as shown in SEQ ID NO: 4; and, an amino acid sequence as shown in SEQ ID NO:

2 or an amino acid sequence having at least 75% identity to the amino acid sequence as shown in SEQ ID NO: 2;

(2) an amino acid sequence as shown in SEQ ID NO: 4 or an amino acid sequence having at least 75% identity to the amino acid sequence as shown in SEQ ID NO: 4; and, an amino acid sequence as shown in SEQ ID NO: 7 or an amino acid sequence having at least 75% identity to the amino acid sequence as shown in SEQ ID NO: 7;

(3) an amino acid sequence as shown in SEQ ID NO: 3 or an amino acid sequence having at least 75% identity to the amino acid sequence as shown in SEQ ID NO: 3; and, an amino acid sequence as shown in SEQ ID NO: 7 or an amino acid sequence having at least 75% identity to the amino acid sequence as shown in SEQ ID NO: 7;

(4) an amino acid sequence as shown in SEQ ID NO: 3 or an amino acid sequence having at least 75% identity to the amino acid sequence as shown in SEQ ID NO: 3; and, an amino acid sequence as shown in SEQ ID NO: 8 or an amino acid sequence having at least 75% identity to the amino acid sequence as shown in SEQ ID NO: 8;

(5) an amino acid sequence as shown in SEQ ID NO: 6 or an amino acid sequence having at least 75% identity to the amino acid sequence as shown in SEQ ID NO: 6; and, an amino acid sequence as shown in SEQ ID NO: 8 or an amino acid sequence having at least 75% identity to the amino acid sequence as shown in SEQ ID NO: 8; or (6) an amino acid sequence as shown in SEQ ID NO: 5 or an amino acid sequence having at least 75% identity to the amino acid sequence as shown in SEQ ID NO: 5; and, an amino acid sequence as shown in SEQ ID NO: 8 or an amino acid sequence having at least 75% identity to the amino acid sequence as shown in SEQ ID NO: 8.

In particular, the antibody or antigen binding fragment thereof provided by the present disclosure comprises at least a heavy chain variable region and a light chain variable region, both comprising the CDRs as described above and framework regions in an arrangement as: FR1-CDR1-FR2-CDR2-FR3-CDR3-FR4. Further alternatively, the up to 25% difference in amino acid sequence due to the “at least 75% identity” may be present in any framework region of the heavy chain variable region or the light chain variable region, or in any domain or sequence in the antibody or antigen binding fragment thereof provided by the present disclosure outside of the heavy chain variable region and the light chain variable region. The difference may result from amino acid deletion, addition or substitution at any position.

The antibody provided by the present disclosure is a murine antibody, a chimeric antibody or a fully or partially humanized antibody; alternatively, the antibody is in the form of a scFv, dsFv, $(dsFv)_2$, Fab, Fab', $F(ab')_2$ or Fv antibody. Preferably, the antibody is a monoclonal antibody or a single chain antibody.

In addition to the variable regions, the antibody or antigen-binding fragment thereof comprises a human or murine constant region, preferably a human or murine heavy chain constant region (CH) and/or light chain constant region (CL). Preferably, the antibody or antigen-binding fragment thereof comprises a heavy chain and a light chain; more preferably, the antibody or antigen binding fragment thereof comprises a heavy chain constant region selected from the group consisting of IgG, IgA, IgM, IgD and IgE and/or a kappa or lambda type light chain constant region. According to one particular embodiment of the invention, the antibody is a monoclonal antibody, preferably a murine, chimeric or humanized monoclonal antibody. According to one particular embodiment of the invention, the monoclonal antibody is an IgG1 antibody.

Further preferably, the antibody or antigen binding fragment thereof provided by the present disclosure comprises a heavy chain constant region comprising an amino acid sequence as shown in SEQ ID NO: 9 or an amino acid sequence having at least 75% identity to the amino acid sequence as shown in SEQ ID NO: 9; and/or a light chain constant region comprising an amino acid sequence as shown in SEQ ID NO: 10 or an amino acid sequence having at least 75% identity to the amino acid sequence as shown in SEQ ID NO: 10.

According to one particular embodiment of the invention, the present disclosure provides a monoclonal antibody having a heavy chain and a light chain comprising respectively:

(1) an amino acid sequence as shown in SEQ ID NO: 13 or an amino acid sequence having at least 75% identity to the amino acid sequence as shown in SEQ ID NO: 13; and, an amino acid sequence as shown in SEQ ID NO: 12 or an amino acid sequence having at least 75% identity to the amino acid sequence as shown in SEQ ID NO: 12;

(2) an amino acid sequence as shown in SEQ ID NO: 13 or an amino acid sequence having at least 75% identity to the amino acid sequence as shown in SEQ ID NO: 13; and, an amino acid sequence as shown in SEQ ID NO: 14 or an amino acid sequence having at least 75% identity to the amino acid sequence as shown in SEQ ID NO: 14;

(3) an amino acid sequence as shown in SEQ ID NO: 15 or an amino acid sequence having at least 75% identity to the amino acid sequence as shown in SEQ ID NO: 15; and, an amino acid sequence as shown in SEQ ID NO: 14 or an amino acid sequence having at least 75% identity to the amino acid sequence as shown in SEQ ID NO: 14;

(4) an amino acid sequence as shown in SEQ ID NO: 15 or an amino acid sequence having at least 75% identity to the amino acid sequence as shown in SEQ ID NO: 15; and, an amino acid sequence as shown in SEQ ID NO: 16 or an amino acid sequence having at least 75% identity to the amino acid sequence as shown in SEQ ID NO: 16;

(5) an amino acid sequence as shown in SEQ ID NO: 17 or an amino acid sequence having at least 75% identity to the amino acid sequence as shown in SEQ ID NO: 17; and, an amino acid sequence as shown in SEQ ID NO: 16 or an amino acid sequence having at least 75% identity to the amino acid sequence as shown in SEQ ID NO: 16; or (6) an amino acid sequence as shown in SEQ ID NO: 18 or an amino acid sequence having at least 75% identity to the amino acid sequence as shown in SEQ ID NO: 18; and, an amino acid sequence as shown in SEQ ID NO: 16 or an amino acid sequence having at least 75% identity to the amino acid sequence as shown in SEQ ID NO: 16.

In another aspect, the present disclosure also provides a nucleic acid molecule comprising a nucleotide sequence encoding the anti-CD22 antibody or antigen-binding fragment thereof provided by the present disclosure, or encoding a heavy chain CDR, a light chain CDR, a heavy chain variable region, a light chain variable region, a heavy chain or a light chain comprised in the anti-CD22 antibody or antigen-binding fragment thereof.

In a further aspect, the present disclosure provides a vector comprising a nucleic acid molecule as described above. The vector can be a eukaryotic expression vector, a prokaryotic expression vector, an artificial chromosome, a phage vector and the like.

In yet a further aspect, the present disclosure provides a host cell comprising a nucleic acid molecule or vector as described above, or a host cell transformed or transfected with a nucleic acid molecule or vector as described above. The host cell may be any prokaryotic or eukaryotic cell, such as a bacterial, insect, fungal, plant or animal cell.

The antibody or antigen binding fragment thereof provided by the present disclosure can be obtained using any method known in the art. For example, the heavy chain variable region and/or the light chain variable region of the antibody, or the heavy chain and/or the light chain of the antibody, may be obtained from the nucleic acid molecule provided by the present disclosure, and then they may be assembled with the optional other domains of the antibody into an antibody; alternatively, the host cell provided by the present disclosure is cultured under conditions that allow the host cell to express the heavy chain variable region and/or the light chain variable region of the antibody or the heavy chain and/or the light chain of the antibody, and to assemble them into an antibody. Optionally, the method further comprises a step of recovering the produced antibody.

In another aspect, the present disclosure also provides a composition comprising an antibody or antigen binding fragment thereof, a nucleic acid molecule, a vector and/or a host cell provided by the present disclosure. Preferably, the composition is a pharmaceutical composition, which further optionally comprises a pharmaceutically acceptable carrier, adjuvant, and excipient.

In yet another aspect, the present disclosure also provides an immunoconjugate comprising the anti-CD22 antibody or antigen binding fragment thereof provided herein and a partner molecule which is a therapeutic agent. The therapeutic agent can be a cytotoxin (e.g., *Pseudomonas aeruginosa* exotoxin (e.g., PE38)), a radioisotope, an antibiotic, a small molecule toxin, other drug, etc.

In addition, the present disclosure also provides a kit comprising an antibody or antigen binding fragment thereof, a nucleic acid molecule, a vector, the host cell, a composition, and/or an immunoconjugate provided by the present disclosure.

In a further aspect, the invention also provides use of an antibody or antigen binding fragment thereof, a nucleic acid molecule, a vector, the host cell, a composition, and/or a immunoconjugate provided herein for the manufacture of a medicament for the treatment of a disease which includes a tumor or cancer expressing CD22. For example, the disease is a CD22-related B cell malignant tumor, or a B cell malignant tumor characterized by high expression of CD22, such as CD22-high expressing lymphoma or leukemia. Preferably, the lymphoma is non-hodgkin's lymphoma, small lymphocytic lymphoma or mantle cell lymphoma; and the leukemia is chronic lymphocytic leukemia, hairy cell leukemia or acute lymphocytic leukemia.

Accordingly, the present disclosure provides a method for treating a disease, comprising administering to a subject in need thereof an antibody or antigen binding fragment thereof, a nucleic acid molecule, a vector, a host cell, a composition, and/or an immunoconjugate provided herein. The subject is a mammal, including a human or non-human primate, and a domestic, farm or laboratory mammal such as dog, cat, cow, pig, sheep, horse, mouse, rabbit, etc. Preferably, the subject is a human. The disease includes a tumor or cancer expressing CD22. For example, the disease is a CD22-related B cell malignant tumor, or a B cell malignant tumor characterized by high expression of CD22, such as CD22 high expressing lymphoma or leukemia. Preferably, the lymphoma is non-hodgkin's lymphoma, small lymphocytic lymphoma or mantle cell lymphoma; and the leukemia is chronic lymphocytic leukemia, hairy cell leukemia or acute lymphocytic leukemia.

BRIEF DESCRIPTION OF THE DRAWINGS

Embodiments of the present invention are described in detail below with reference to the attached figures, in which.

DETAILED DESCRIPTION OF PREFERRED EMBODIMENTS

Figure 1:
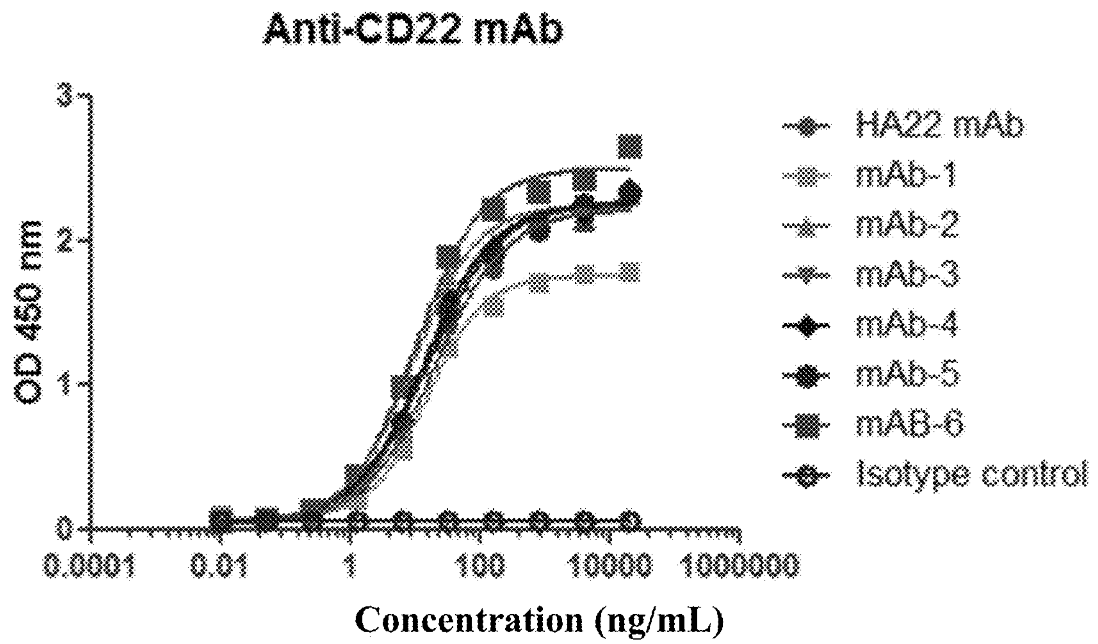
FIG. 1 shows detection results of binding of the antibodies provided by the present disclosure to CD22 by ELISA.

The invention is illustrated below with reference to specific examples. It will be understood by those skilled in the art that these examples are merely illustrative of the invention and do not limit the scope of the invention in any way.

Experimental procedures in the following examples are all conventional ones, unless otherwise specified. Raw materials and reagents used in the following examples are all commercially available products, unless otherwise specified.

Example 1 Construction and Preparation of the Antibodies

In this Example, an IgG1-type monoclonal antibody was reconstructed by obtaining VH and VL region sequences and fusing them to constant regions.

1.1 Humanization Design

A framework shuffling strategy was used to alter amino acids in the framework regions of heavy chain variable region ($V_H$) and light chain variable region ($V_L$) comprised in the recombinant immunotoxin HA22 from the original murine to human ones. All the CDRs, which were determined using both the Kabat and Chothia numbering systems and the online tool (www.bioinf.org.uk/abs/), were left unchanged. Each of the framework and J regions in both the VH and VL of HA22 was aligned to the human antibody germline sequences in the international ImMunoGeneTics information System® (international protein-protein interaction database) (IMGT: www.imgt.org) for the closest human antibody matches. Murine residues that were deemed as Vernier residues or important for VH/VL interactions were not changed to preserve the specificity and affinity towards CD22.

A panel of humanization designs were prepared and evaluated to select the final candidate that possessed maximum humanization while maintaining optimal affinity and efficacy profile.

1.2 Gene Sequence Determination

Amino acid sequences of the heavy chain variable region (VH) and light chain variable region (VL) contained in HA22 and humanized versions of the antibody are shown in Table 1. Elbow regions of the heavy and light chains were determined through defining antibody variable regions according to Kabat nomenclature, for subsequent mAb reconstruction; and CDR1, CDR2, and CDR3 were identified and underlined.

TABLE 1

V region sequences in the heavy and light chains (CDRs are underlined)

| Name | Sequence |
|---|---|
| HA22 VH | EVQLVESGGGLVKPGGSLKLSCAASGFAFS**IYDMS**WVRQTP<br>EKCLEWVA**YISSGGGTTYYPDTVKG**RFTISRDNAKNTLYLQ<br>MSSLKSEDTAMYYCAR**HSGYGTHWGVLFAY**WGQGTLVTVSA<br>(SEQ ID NO: 1) |
| HA22 VL | DIQMTQTTSSLSASLGDRVTISC**RASQDISNYLN**WYQQKPD<br>GTVKLLIY**YTSILHS**GVPSRFSGSGSGTDYSLTISNLEQED<br>FATYFC**QQGNTLPWT**FGCGTKLEIK<br>(SEQ ID NO: 2) |
| VH1 | EVQLVESGGGLVKPGGSLRLSCAASGFAFS**IYDMS**WVRQAP<br>GKCLEWVA**YISSGGGTTYYPDSVKG**RFTISRENAKNSLYLQ<br>MNSLKSEDTAMYYCAR**HSGYGTHWGVLFAY**WGQGTMVTVSS<br>(SEQ ID NO: 3) |
| VH2 | EVQLVESGGGLVKPGGSLRLSCAASGFAFS**IYDMS**WVRQTP<br>EKCLEWVA**YISSGGGTTYYPDSVKG**RFTISRENAKNSLYLQ<br>MNSLKSEDTAMYYCAR**HSGYGTHWGVLFAY**WGQGTMVTVSS<br>(SEQ ID NO: 4) |
| VH4 | EVQLVESGGGLVKPGGSLRLSCAASGFAFS**IYDMS**WIRQAP<br>GKCLEWVA**YISSGGGTTYYPGSVKG**RFTISRENAKNSLYLQ<br>MNSLRAGDTAVYYCAR**HSGYGTHWGVLFAY**WGQGTMVTVSS<br>(SEQ ID NO: 5) |

TABLE 1-continued

V region sequences in the heavy and light chains (CDRs are underlined)

| Name | Sequence |
|---|---|
| VH5 | EVQLVESGGGLVKPGGSLRLSCAASGFAFS**IYDMS**WIRQAP<br>GKCLEWVA**YISSGGGTTYYPGSVKG**RFTISRENAKNSLYLQ<br>MNSLRSEDTAVYYCAR**HSGYGTHWGVLFAY**WGQGTMVTVSS<br>(SEQ ID NO: 6) |
| VL-2 | DIQMTQSTSTLSASVGDRVTITC**RASQDISNYLN**WYQQRPD<br>GSVKLLIY**YTSILHS**GVPSRFSGSGSGTDYTLTISSLQDED<br>FATYFC**QQGNTLPWT**FGCGTKVEIK<br>(SEQ ID NO: 7) |
| VL-4 | DIQMTQSPSTLSASVGDRVTITC**RASQDISNYLN**WFQQRPG<br>QSPRLLIY**YTSILHS**GVPSRFSGSGSGTDYTLTISSLQPED<br>FATYYC**QQGNTLPWT**FGCGTKVEIK<br>(SEQ ID NO: 8) |

1.3 Amino Acid Sequences of Constant Regions of IgG1

The antibody was determined to have a kappa-type light chain upon an analysis of the variable regions, so kappa-type light chain constant region and IgG1 heavy chain constant region were selected for the reconstruction of IgG antibodies. The constant region sequences are shown in Table 2.

TABLE 2

Constant region sequences

| Name | Sequence |
|---|---|
| CL | RTVAAPSVFIFPPSDEQLKSGTASVVCLLNNFYPREAKVQ<br>WKVDNALQSGNSQESVTEQDSKDSTYSLSSTLTLSKADYE<br>KHKVYACEVTHQGLSSPVTKSFNRGEC<br>(SEQ ID NO: 9) |
| CH1 + Fc | ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKKVEPKSCDKTHTCPPCPAPELLGG<br>PSVFLFPPKPKDTLMISRTPEVTCVVVDVSHEDPEVKFNW<br>YVDGVEVHNAKTKPREEQYNSTYRVVSVLTVLHQDWLNGK<br>EYKCKVSNKALPAPIEKTISKAKGQPREPQVYTLPPSRDE<br>LTKNQVSLTCLVKGFYPSDIAVEWESNGQPENNYKTTPPV<br>LDSDGSFFLYSKLTVDKSRWQQGNVFSCSVMHEALHNHYT<br>QKSLSLSPGK<br>(SEQ ID NO: 10) |

1.4 Reconstructed IgG Monoclonal Antibodies

Complete heavy and light chains shown in Table 3 were reconstructed through fusing the V region sequences provided in Table 1 to the constant region sequences provided in Table 2.

TABLE 3

Amino acid sequences of the reconstructed IgG antibodies (CDRs are underlined and constant regions are in italics)

| Name | Combination | Sequence |
|---|---|---|
| HA22 mAb | HA22 HC | EVQLVESGGGLVKPGGSLKLSCAASGFAFSIYDMSWVRQ<br>TPEKCLEWVAYISSGGGTTYYPDTVKGRFTISRDNAKNT<br>LYLQMSSLKSEDTAMYYCARHSGYGTHWGVLFAYWGQ<br>GTLVTVSA*ASTKGPSVFPLAPSSKSTSGGTAALGCLVKDYFP*<br>*EPVTVSWNSGALTSGVHTFPAVLQSSGLYSLSSVVTVPSSSLG*<br>*TQTYICNVNHKPSNTKVDKKVEPKSCDKTHTCPPCPAPELL*<br>*GGPSVFLFPPKPKDTLMISRTPEVTCVVVDVSHEDPEVKFN*<br>*WYVDGVEVHNAKTKPREEQYNSTYRVVSVLTVLHQDWLNG*<br>*KEYKCKVSNKALPAPIEKTISKAKGQPREPQVYTLPPSRDEL*<br>*TKNQVSLTCLVKGFYPSDIAVEWESNGQPENNYKTTPPVLDS*<br>*DGSFFLYSKLTVDKSRWQQGNVFSCSVMHEALHNHYTQKS*<br>*LSLSPGK* (SEQ ID NO: 11) |
| | HA22 LC | DIQMTQTTSSLSASLGDRVTISCRASQDISNYLNWYQQK |

TABLE 3-continued

Amino acid sequences of the reconstructed IgG antibodies (CDRs are underlined and constant regions are in italics)

| Name | Combination | Sequence |
|---|---|---|
| | | PDGTVKLLIYYTSILHSGVPSRFSGSGSGTDYSLTISNLEQ EDFATYFCQQGNTLPWTFGCGTKLEIK*RTVAAPSVFIFPPS DEQLKSGTASVVCLLNNFYPREAKVQWKVDNALQSGNSQES VTEQDSKDSTYSLSSTLTLSKADYEKHKVYACEVTHQGLSSP VTKSFNRGEC* (SEQ ID NO: 12) |
| mAb-1 | V2 HC | EVQLVESGGGLVKPGGSLRLSCAASGFAFSIYDMSWVRQ TPEKCLEWVAYISSGGGTTYYPDSVKGRFTISRENAKNSL YLQMNSLKSEDTAMYYCARHSGYGTHWGVLFAYWGQ GTMVTVSS*ASTKGPSVFPLAPSSKSTSGGTAALGCLVKDYF PEPVTVSWNSGALTSGVHTFPAVLQSSGLYSLSSVVTVPSSSL GTQTYICNVNHKPSNTKVDKKVEPKSCDKTHTCPPCPAPEL LGGPSVFLFPPKPKDTLMISRTPEVTCVVVDVSHEDPEVKF NWYVDGVEVHNAKTKPREEQYNSTYRVVSVLTVLHQDWLN GKEYKCKVSNKALPAPIEKTISKAKGQPREPQVYTLPPSRDE LTKNQVSLTCLVKGFYPSDIAVEWESNGQPENNYKTTPPVL DSDGSFFLYSKLTVDKSRWQQGNVFSCSVMHEALHNHYTQ KSLSLSPGK* (SEQ ID NO: 13) |
| | HA22 LC | DIQMTQTTSSLSASLGDRVTISCRASQDISNYLNWYQQK PDGTVKLLIYYTSILHSGVPSRFSGSGSGTDYSLTISNLEQ EDFATYFCQQGNTLPWTFGCGTKLEIK*RTVAAPSVFIFPPS DEQLKSGTASVVCLLNNFYPREAKVQWKVDNALQSGNSQES VTEQDSKDSTYSLSSTLTLSKADYEKHKVYACEVTHQGLSSP VTKSFNRGEC* (SEQ ID NO: 12) |
| mAb-2 | V2 HC | EVQLVESGGGLVKPGGSLRLSCAASGFAFSIYDMSWVRQ TPEKCLEWVAYISSGGGTTYYPDSVKGRFTISRENAKNSL YLQMNSLKSEDTAMYYCARHSGYGTHWGVLFAYWGQ GTMVTVSS*ASTKGPSVFPLAPSSKSTSGGTAALGCLVKDYF PEPVTVSWNSGALTSGVHTFPAVLQSSGLYSLSSVVTVPSSSL GTQTYICNVNHKPSNTKVDKKVEPKSCDKTHTCPPCPAPEL LGGPSVFLFPPKPKDTLMISRTPEVTCVVVDVSHEDPEVKF NWYVDGVEVHNAKTKPREEQYNSTYRVVSVLTVLHQDWLN GKEYKCKVSNKALPAPIEKTISKAKGQPREPQVYTLPPSRDE LTKNQVSLTCLVKGFYPSDIAVEWESNGQPENNYKTTPPVL DSDGSFFLYSKLTVDKSRWQQGNVFSCSVMHEALHNHYTQ KSLSLSPGK* (SEQ ID NO: 13) |
| | V2 LC | DIQMTQSTSTLSASVGDRVTITCRASQDISNYLNWYQQR PDGSVKLLIYYTSILHSGVPSRFSGSGSGTDYTLTISSLQD EDFATYFCQQGNTLPWTFGCGTKVEIK*RTVAAPSVFIFPPS DEQLKSGTASVVCLLNNFYPREAKVQWKVDNALQSGNSQES VTEQDSKDSTYSLSSTLTLSKADYEKHKVYACEVTHQGLSSP VTKSFNRGEC* (SEQ ID NO: 14) |
| mAb-3 | V1 HC | EVQLVESGGGLVKPGGSLRLSCAASGFAFSIYDMSWVRQ APGKCLEWVAYISSGGGTTYYPDSVKGRFTISRENAKNS LYLQMNSLKSEDTAMYYCARHSGYGTHWGVLFAYWGQ GTMVTVSS*ASTKGPSVFPLAPSSKSTSGGTAALGCLVKDYF PEPVTVSWNSGALTSGVHTFPAVLQSSGLYSLSSVVTVPSSSL GTQTYICNVNHKPSNTKVDKKVEPKSCDKTHTCPPCPAPEL LGGPSVFLFPPKPKDTLMISRTPEVTCVVVDVSHEDPEVKF NWYVDGVEVHNAKTKPREEQYNSTYRVVSVLTVLHQDWLN GKEYKCKVSNKALPAPIEKTISKAKGQPREPQVYTLPPSRDE LTKNQVSLTCLVKGFYPSDIAVEWESNGQPENNYKTTPPVL DSDGSFFLYSKLTVDKSRWQQGNVFSCSVMHEALHNHYTQ KSLSLSPGK* (SEQ ID NO: 15) |
| | V2 LC | DIQMTQSTSTLSASVGDRVTITCRASQDISNYLNWYQQR PDGSVKLLIYYTSILHSGVPSRFSGSGSGTDYTLTISSLQD EDFATYFCQQGNTLPWTFGCGTKVEIK*RTVAAPSVFIFPPS DEQLKSGTASVVCLLNNFYPREAKVQWKVDNALQSGNSQES VTEQDSKDSTYSLSSTLTLSKADYEKHKVYACEVTHQGLSSP VTKSFNRGEC* (SEQ ID NO: 14) |
| mAb-4 | V1 HC | EVQLVESGGGLVKPGGSLRLSCAASGFAFSIYDMSWVRQ APGKCLEWVAYISSGGGTTYYPDSVKGRFTISRENAKNS LYLQMNSLKSEDTAMYYCARHSGYGTHWGVLFAYWGQ GTMVTVSS*ASTKGPSVFPLAPSSKSTSGGTAALGCLVKDYF PEPVTVSWNSGALTSGVHTFPAVLQSSGLYSLSSVVTVPSSSL GTQTYICNVNHKPSNTKVDKKVEPKSCDKTHTCPPCPAPEL LGGPSVFLFPPKPKDTLMISRTPEVTCVVVDVSHEDPEVKF NWYVDGVEVHNAKTKPREEQYNSTYRVVSVLTVLHQDWLN GKEYKCKVSNKALPAPIEKTISKAKGQPREPQVYTLPPSRDE LTKNQVSLTCLVKGFYPSDIAVEWESNGQPENNYKTTPPVL DSDGSFFLYSKLTVDKSRWQQGNVFSCSVMHEALHNHYTQ KSLSLSPGK* (SEQ ID NO: 15) |

TABLE 3-continued

Amino acid sequences of the reconstructed IgG antibodies (CDRs are underlined and constant regions are in italics)

| Name | Combination | Sequence |
| --- | --- | --- |
| | V4 LC | DIQMTQSPSTLSASVGDRVTITCRASQDISNYLNWFQQRP<br>GQSPRLLIYYTSILHSGVPSRFSGSGSGTDYTLTISSLQPE<br>DFATYYCQQGNTLPWTFGCGTKVEIKRTVAAPSVFIFPPS<br>DEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC (SEQ ID NO: 16) |
| mAb-5 | V5 HC | EVQLVESGGGLVKPGGSLRLSCAASGFAFSIYDMSWIRQ<br>APGKCLEWVAYISSGGGTTYYPGSVKGRFTISRENAKNS<br>LYLQMNSLRSEDTAVYYCARHSGYGTHWGVLFAYWGQ<br>GTMVTVSSASTKGPSVFPLAPSSKSTSGGTAALGCLVKDYF<br>PEPVTVSWNSGALTSGVHTFPAVLQSSGLYSLSSVVTVPSSSL<br>GTQTYICNVNHKPSNTKVDKKVEPKSCDKTHTCPPCPAPEL<br>LGGPSVFLFPPKPKDTLMISRTPEVTCVVVDVSHEDPEVKF<br>NWYVDGVEVHNAKTKPREEQYNSTYRVVSVLTVLHQDWLN<br>GKEYKCKVSNKALPAPIEKTISKAKGQPREPQVYTLPPSRDE<br>LTKNQVSLTCLVKGFYPSDIAVEWESNGQPENNYKTTPPVL<br>DSDGSFFLYSKLTVDKSRWQQGNVFSCSVMHEALHNHYTQ<br>KSLSLSPGK (SEQ ID NO: 17) |
| | V4 LC | DIQMTQSPSTLSASVGDRVTITCRASQDISNYLNWFQQRP<br>GQSPRLLIYYTSILHSGVPSRFSGSGSGTDYTLTISSLQPE<br>DFATYYCQQGNTLPWTFGCGTKVEIKRTVAAPSVFIFPPS<br>DEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC (SEQ ID NO: 16) |
| mAb-6 | V4 HC | EVQLVESGGGLVKPGGSLRLSCAASGFAFSIYDMSWIRQ<br>APGKCLEWVAYISSGGGTTYYPGSVKGRFTISRENAKNS<br>LYLQMNSLRAGDTAVYYCARHSGYGTHWGVLFAYWGQ<br>GTMVTVSSASTKGPSVFPLAPSSKSTSGGTAALGCLVKDYF<br>PEPVTVSWNSGALTSGVHTFPAVLQSSGLYSLSSVVTVPSSSL<br>GTQTYICNVNHKPSNTKVDKKVEPKSCDKTHTCPPCPAPEL<br>LGGPSVFLFPPKPKDTLMISRTPEVTCVVVDVSHEDPEVKF<br>NWYVDGVEVHNAKTKPREEQYNSTYRVVSVLTVLHQDWLN<br>GKEYKCKVSNKALPAPIEKTISKAKGQPREPQVYTLPPSRDE<br>LTKNQVSLTCLVKGFYPSDIAVEWESNGQPENNYKTTPPVL<br>DSDGSFFLYSKLTVDKSRWQQGNVFSCSVMHEALHNHYTQ<br>KSLSLSPGK (SEQ ID NO: 18) |
| | V4 LC | DIQMTQSPSTLSASVGDRVTITCRASQDISNYLNWFQQRP<br>GQSPRLLIYYTSILHSGVPSRFSGSGSGTDYTLTISSLQPE<br>DFATYYCQQGNTLPWTFGCGTKVEIKRTVAAPSVFIFPPS<br>DEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC (SEQ ID NO: 16) |

1.5 Preparation of the Monoclonal Antibodies pCDNA 3.4 vector was used as the expression vector for the mAbs. After codon optimization, full genes were synthesized and inserted into the pCDNA 3.4 vector and expression vectors for transfection were prepared using endotoxin-free plasmid preparation kit. ExpicCHO cell strain was used as a host for transient expression host. After transient transfection, cell culture supernatants were harvested, and antibodies were obtained through affinity purification, and then identified and stored at −80° C.

Example 2 Detection of Binding of the Antibodies to CD22 Antigen

In this Example, ELISA plates were coated with CD22 antigen to capture antibodies to be evaluated, and the color developed through an HRP-labeled secondary antibody capable of specifically recognizing Fd region, and the binding ($EC_{50}$) of each mAb to the CD22 antigen was detected.

ELISA plates were coated with 200 ng/mL CD22 antigen (Biotinylated Human Siglec-2/CD22 Protein, Fc, Avitag™, ACROBiosystems (ARCO)) at 100 μl per well, at 4° C. overnight. Next day, the plates were washed with PBST, then blocked by the added blocking buffer (PBST+3% milk) at 37° C. for 1-2 hours, and then washed again with PBST.

Each antibody to be tested was diluted with PBST+1% BSA in gradient, to obtain antibody dilutions at concentrations of 0.01 ng/mL, 0.05 ng/mL, 0.25 ng/ml, 1.28 ng/ml, 6.40 ng/ml, 32 ng/ml, 160 ng/ml, 800 ng/mL, 4000 ng/mL, 20000 ng/mL, respectively; and 100 μl of each of the dilutions was added to each well of the ELISA plates which were then incubated at 37° C. for 1 hour.

After incubation, the plates were washed with PBST. 100 μl of 1:10000 diluted secondary antibody (Mouse anti-human IgG Fd secondary antibody, HRP; REF: SA5-10190, Invitrogen, USA) was added to each well of the ELISA plates which were then incubated at 37° C. for 1 hour. Thereafter, the plates were washed with PBST.

100 μl of TMB solution (TMB Single-Component Substrate solution, Cat #PR1200, Beijing Solarbio Science & Technology Co., Ltd.) was added to each well of the plates which were then incubated at room temperature for 15 minutes. Then 50 μl of stop buffer (ELISA stop buffer (10×), Cat #C1058, Beijing Solarbio Science & Technology Co., Ltd.) was added thereto, and the plates were shaken. Absorbance values at 450 nm were detected. Results are shown in FIG. 1 and Table 4.

As shown in FIG. 1 and Table 4, the OD450 value of the isotype control was below 0.1, indicating no interference on the results due to non-specific binding; the fitting degree of 4-parameter non-linear fitting was greater than 0.99, an excellent fitting degree, indicating the results can be analyzed objectively. The Top values showed mAb-6 exhibited a remarkable high signal value, reaching 2.435-2.564, which was significantly higher than the value 2.147-2.283 of HA22 mAb, indicating that mAb-6 has a higher plateau of saturation binding; the Top value of mAb-1 was 1.726-1.795, significantly lower than 2.147-2.283 of HA22 mAb; and the Top values of the remaining mAb-2, mAb-3, mAb-4, and mAb-5 were comparable to or slightly higher than that of HA22 mAb.

$EC_{50}$ value of the positive antibody HA22 mAb was 20.28 ng/mL, and $EC_{50}$ values of mAb-1 to mAb-6 were all lower than that of HA22 mAb, and the $EC_{50}$ values can be ranked as follows: mAb-2<mAb-6<mAb-3<mAb-4<mAb-1<mAb-5<HA22 mAb.

TABLE 4

Detection results of binding of the antibodies to CD22 antigen by ELISA

| $EC_{50}$ (ng/mL) | | R2 | | Top | |
|---|---|---|---|---|---|
| HA22 mAb | 20.28 | HA22 mAb | 0.9935 | HA22 mAb | 2.147-2.283 |
| mAb-1 | 15.40 | mAb-1 | 0.9964 | mAb-1 | 1.726-1.795 |
| mAb-2 | 9.057 | mAb-2 | 0.9961 | mAb-2 | 2.202-2.293 |
| mAb-3 | 13.91 | mAb-3 | 0.9954 | mAb-3 | 2.176-2.278 |
| mAb-4 | 13.92 | mAb-4 | 0.9927 | mAb-4 | 2.191-2.329 |
| mAb-5 | 16.35 | mAb-5 | 0.9962 | mAb-5 | 2.221-2.325 |
| mAb-6 | 10.44 | mAb-6 | 0.9942 | mAb-6 | 2.435-2.564 |
| Isotype control | 0.1545 | Isotype control | 0.1733 | Isotype control | 0.05848-0.06417 |

Example 3 Study on Binding Kinetics of the Antibodies to CD22 Antigen

In this Example, the binding kinetics of the antibodies to the antigen was detected by SPR.

Following reagents and materials were mainly used:

Antigen to be immobilized: CD22-Fc-biotinylated antigen: ACROBiosystems (ARCO)) SI2-H82F8;

Antibodies to be tested: Anti-CD22 mAbs;

Chip SA;

Immobilization buffer: (1) 1 M NaCl/50 mM NaOH; (2) 1 M NaCl/50 mM NaOH/50% isopropanol;

Running buffer: 1×HBS-EP buffer;

Regeneration buffer: Glycine, pH 1.5.

Experimental steps were as follows:

1) A sensor chip SA was taken and its surface was cleaned with ultrapure water; and after dried under nitrogen, was inserted into the slot. The immobilization buffers (1) and (2) were added to the columns A1 and A2 in a 96 well plate, and 3.85 nM CD22-Fc-biotinylated antigen were added at 200 μL per well into corresponding wells in column A3, respectively. The program was set to immobilize the antigen, and the immobilization was stopped when delta RU of about 70 RU was achieved.

2) Program "binding test" was set, including association time of 250 s and dissociation time of 600 s, and a test was performed using HA22 mAb, a dissociation degree of 4-5% was shown.

3) The HA22 mAb was diluted to 1000 nM and subsequently to 100 nM, and further 2-fold diluted starting from 100 nM for 8 times, at a final volume of about 250 μL per well. The program was set up to detect the binding capacity of that antibody No. 1 to the antigen, with association time of 250 s and dissociation time of 600 s. The analysis software showed the binding of the HA22 mAb was fitted normally.

4) All the antibodies, i.e., mAb-1 to mAb-6, were diluted to 1000 nM and subsequently to 100 nM, and further 2-fold diluted starting from 100 nM for 8 times, at a final volume of about 250 μL per well. The same program as that in step 3 was set up to detect affinity in batches. Results were analyzed using Biacore 8K evaluation.

Figure 2:
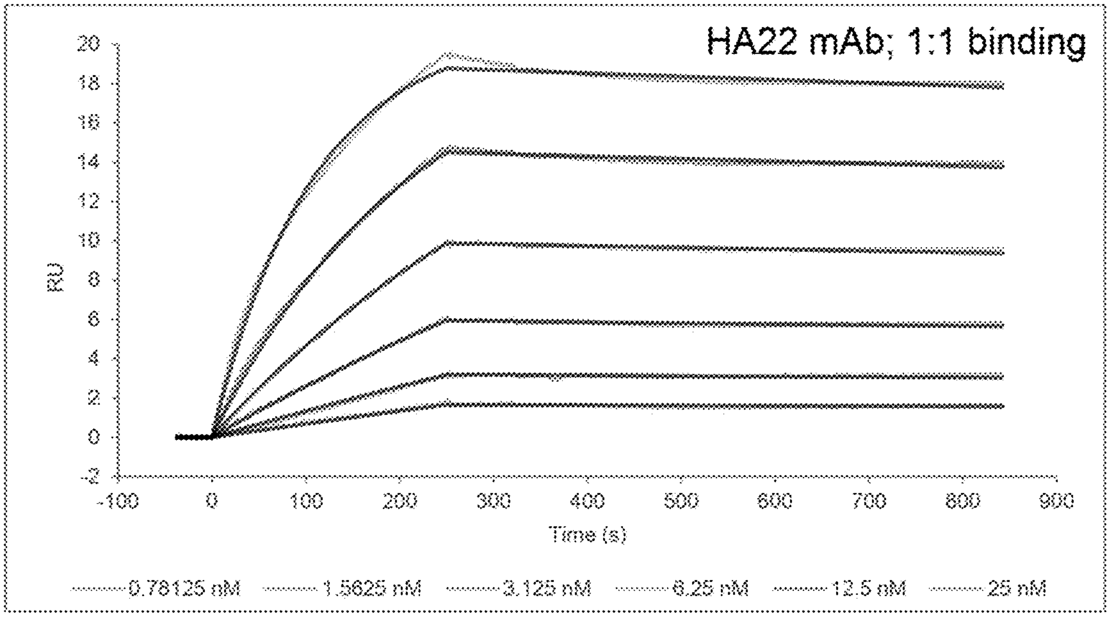
FIG. 2 shows detection results of binding kinetics of the antibodies provided by the present disclosure to CD22 by SPR using 1:1 binding model, in which panel 2A: HA22 mAb; panel 2B: mAb-1; panel 2C: mAb-2; panel 2D: mAb-3; panel 2E: mAb-4; panel 2F: mAb-5; and panel 2G: mAb-6.
Figure 2:
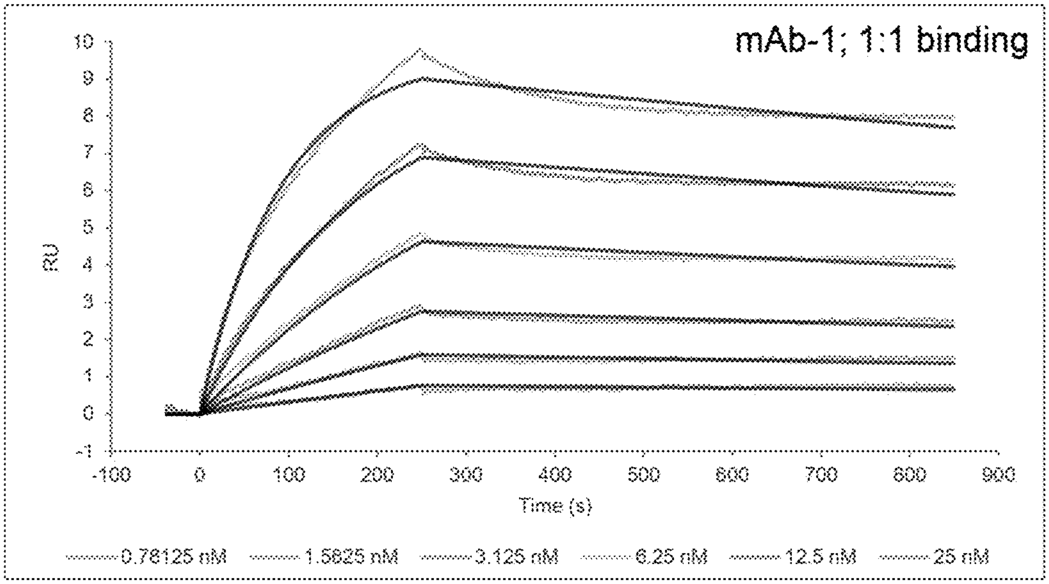
Figure 2:
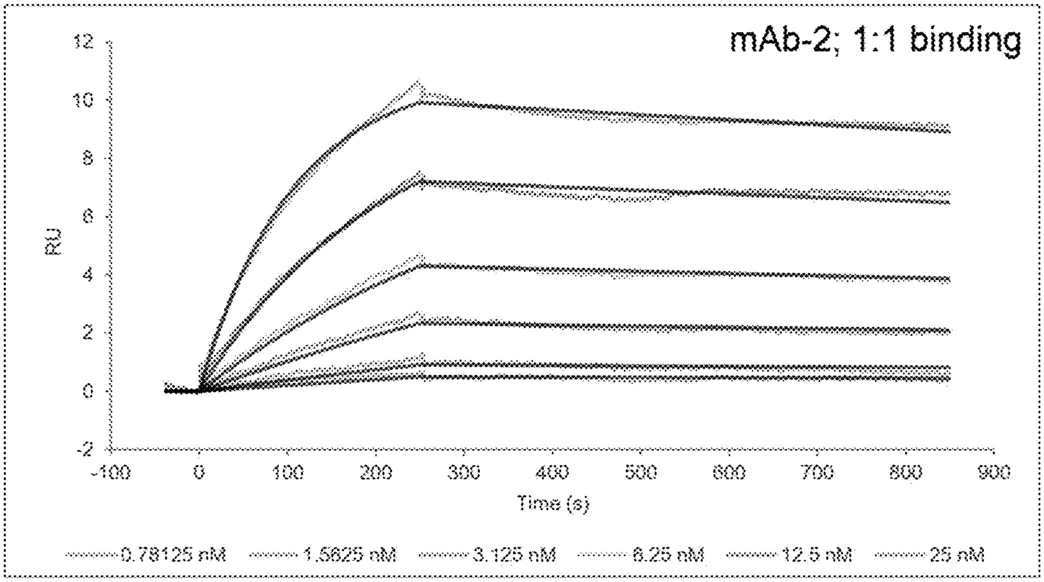
Figure 2:
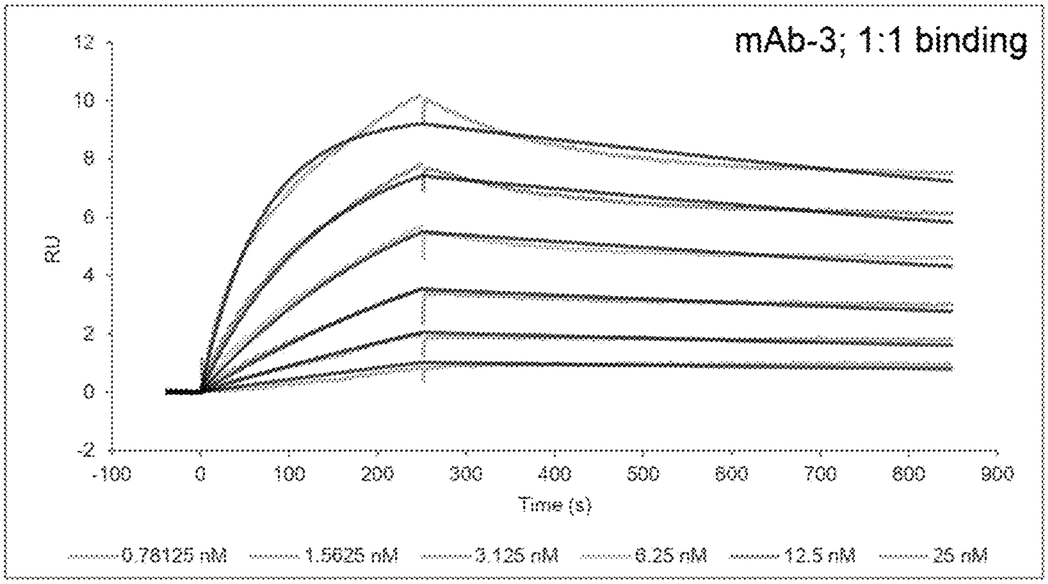
Figure 2:
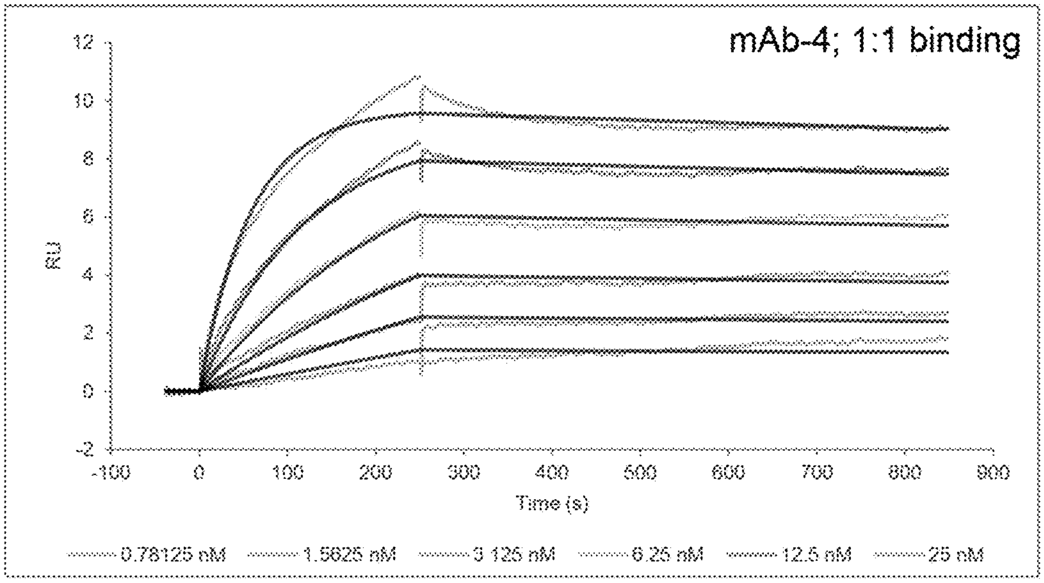
Figure 2:
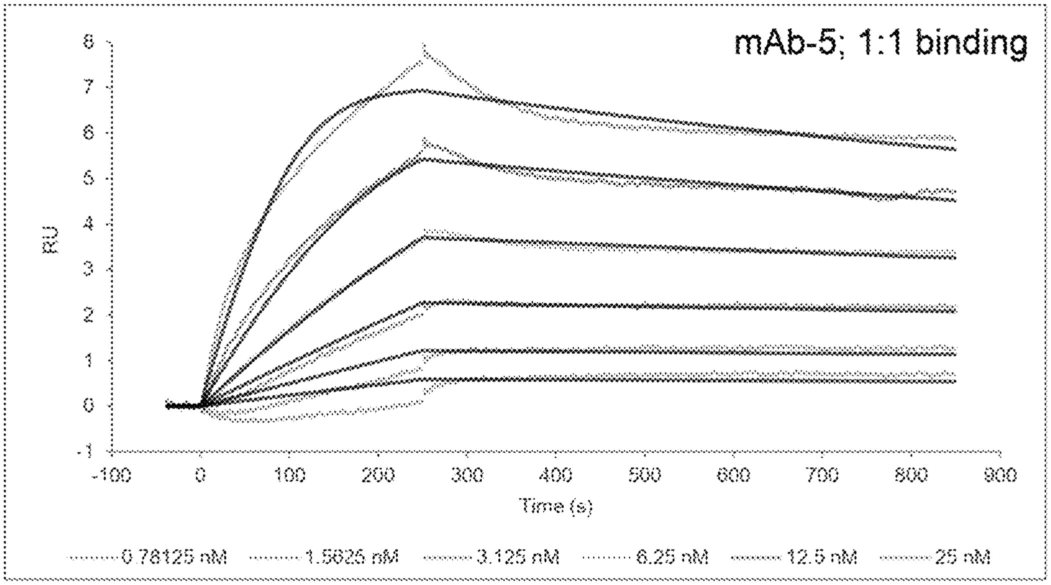
Figure 2:
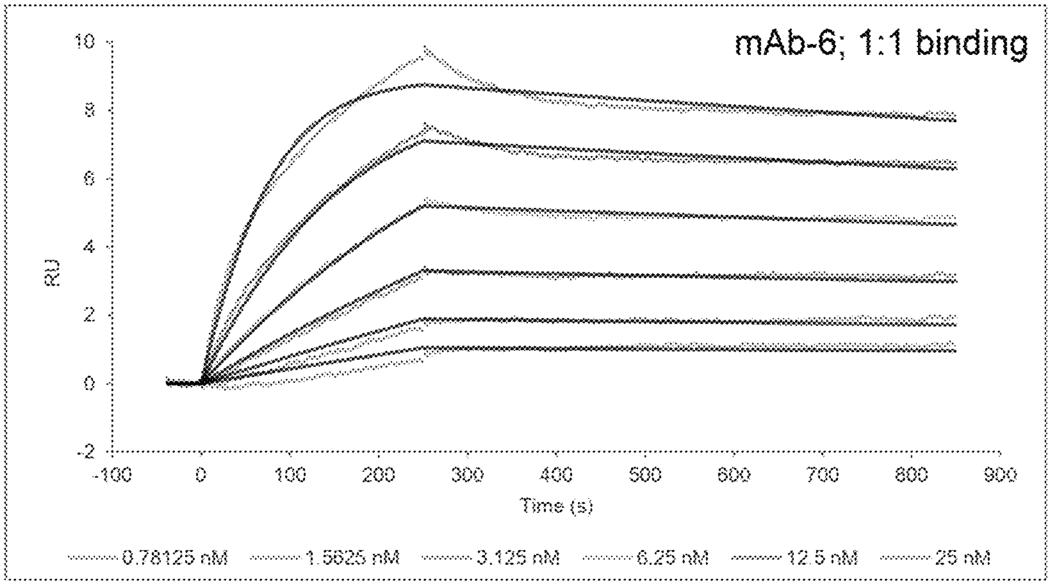

The results are shown in FIG. 2 and Table 5.

TABLE 5

Results of SPR analysis of antibody affinity

| Antibody | Quality Kinetics $Chi^2$ ($RU^2$) | 1:1 Binding Ka (1/Ms) | Kd (1/s) | KD (M) |
|---|---|---|---|---|
| HA22 mAb | 1.91E−02 | 3.70E+05 | 8.93E−05 | 2.42E−10 |
| mAb-1 | 2.26E−02 | 4.34E+05 | 2.62E−04 | 6.04E−10 |
| mAb-2 | 2.30E−02 | 3.76E+05 | 1.77E−04 | 4.70E−10 |
| mAb-3 | 3.15E−02 | 5.67E+05 | 4.04E−04 | 7.13E−10 |
| mAb-4 | 5.75E−02 | 6.85E+05 | 9.91E−05 | 1.45E−10 |
| mAb-5 | 3.76E−02 | 1.08E+06 | 4.11E−04 | 3.82E−10 |
| mAb-6 | 3.10E−02 | 6.99E+05 | 2.20E−04 | 3.15E−10 |

Example 4 Study on Binding of the Antibodies to CD22-Positive Cell Lines

Raji cells (having a relatively high expression of CD22), CA46 cells (having a relatively high expression of CD22), and REH cells (having a relatively medium expression of CD22) were selected, and the cell binding ability of the antibodies was evaluated by curves of mean fluorescence intensity versus concentration obtained through flow cytometry (FACS).

Reagents:

FACS Buffer: 2% FBS+PBS;

Goat anti-Human IgG (H+L) Secondary Antibody, FITC: Invitrogen, Catalogue number 31529;

4% PFA;

Allophycayanin (APC) AffiniPure $F(ab')_2$ Fragment Goat Anti-Human IgG, Fcγ fragment specific, Jackson Immunoresearch, Catalogue number: 109-136-170.

Experimental steps were as follows:

1) Raji, CA46 and REH cells in logarithmic growth phase were harvested, and centrifuged at 1,000 rpm for 3 min.

2) The cells were washed twice with FACS Buffer (2% FBS+PBS), by centrifugation at 1,000 rpm for 3 min.

3) The cells were resuspended in FACS Buffer, and the cell density was adjusted to 2E6/mL.

4) The cell suspensions were added into 96 well round-bottom plates, at 50 μL per well, which were then placed on ice.

5) Each of the antibodies to be detected were 5-fold diluted serially to 8 concentrations: 100 μg/mL, 20 μg/mL, 4 μg/mL, 0.8 μg/mL, 0.16 μg/mL, 0.032 μg/mL, 0.0064 μg/mL and 0.00128 μg/mL.

6) The diluted antibodies were added into the wells containing cells at a 1:1 ratio by volume, to obtain final concentrations of 50 μg/mL, 10 μg/mL, 2 μg/mL, 0.4 μg/mL, 0.08 μg/mL, 0.016 μg/mL, 0.0032 μg/mL, 0.00064 μg/mL, and mixed with the cell suspensions, and the plates were then placed on ice in a 37° C. refrigerator and incubated for 30 min.

7) After the incubation, the cells were taken out and centrifuged at 2,000 rpm for 3 min.

8) The cells were washed twice with FACS Buffer, by centrifugation at 2,000 rpm for 3 min.

9) The cells were fixed with 2% PFA for 20 min at room temperature.

10) The cells were washed twice with FACS Buffer, by centrifugation at 2,000 rpm for 3 min.

11) The secondary antibodies (Goat anti-Human IgG (H+L) Secondary Antibody, FITC was used for Raji cells and REH cells; and Allophycayanin (APC) AffiniPure F(ab')$_2$ Fragment Goat Anti-Human IgG, Fcγ fragment specific was used for CA46 cells) were formulated at 1:800 in buffers, and 100 μL of each were added into the cells, and the plates were then placed on ice in a 4° C. refrigerator and incubated for 30 min.

12) After the incubation, the cells were centrifuged at 2,000 rpm for 3 min.

13) Supernatants were discarded, and the cells were washed twice with FACS Buffer, by centrifugation at 2,000 rpm for 3 min.

14) The cells were suspended in 200 μL of FACS Buffer, and fluorescence intensity of FITC and fluorescence intensity of APC were detected.

Figure 3:
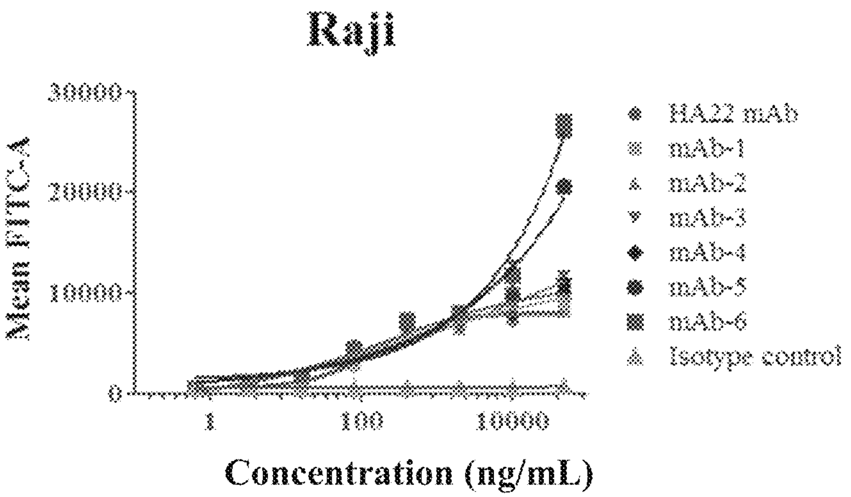
FIG. 3 shows detection results of binding of the antibodies provided by the present disclosure to CD22 on cell membrane by flow cytometry (FACS), in which panel 3A: Raji cells; panel 3B: REH cells; and panel 3C: CA46 cells.
Figure 3:
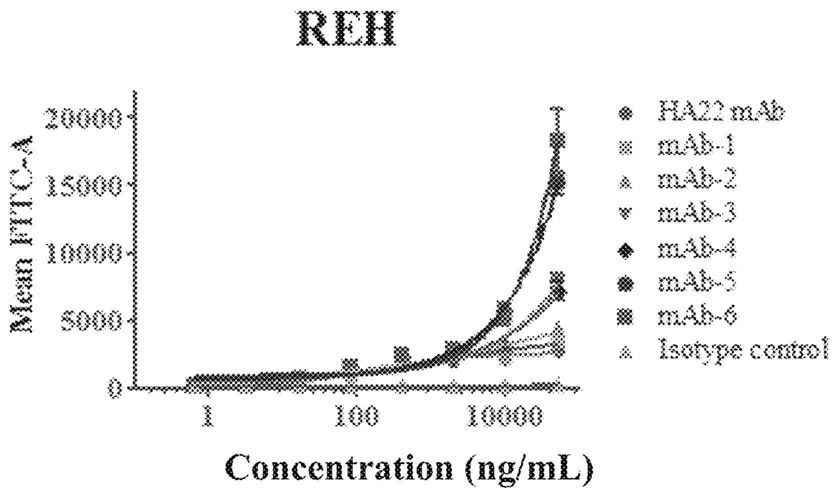
Figure 3:
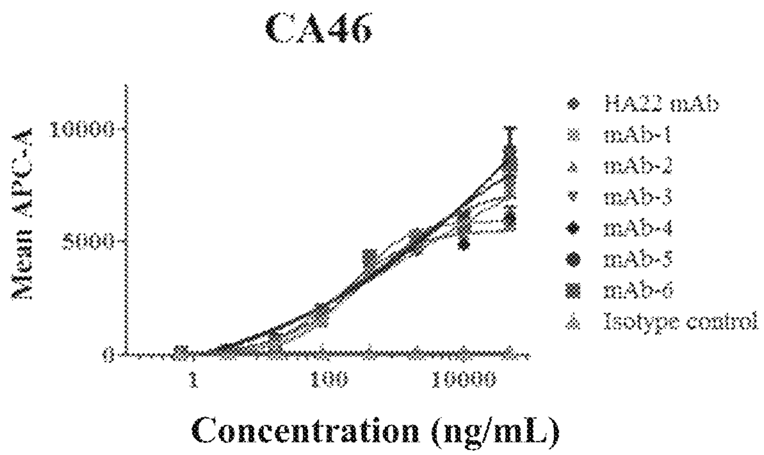

Results are shown in FIG. 3 and Tables 6-1 to 6-3.

TABLE 6-1

Detection results of binding of the antibodies to CD22 on the cell membrane of Raji cells by FACS

| | R2 | | Top | | $EC_{50}$ (ng/mL) |
|---|---|---|---|---|---|
| HA22 mAb | 0.9888 | HA22 mAb | 7506-8131 | HA22 mAb | 152.0 |
| mAb-1 | 0.9777 | mAb-1 | 7594-8558 | mAb-1 | 151.6 |
| mAb-2 | 0.9546 | mAb-2 | 5072-19663 | mAb-2 | 276.2 |
| mAb-3 | 0.9659 | mAb-3 | (very wide) | mAb-3 | ~1.355e+022 |
| mAb-4 | 0.9572 | mAb-4 | 8407-13897 | mAb-4 | 206.3 |
| mAb-5 | 0.9467 | mAb-5 | (very wide) | mAb-5 | ~1.362e+017 |
| mAb-6 | 0.9646 | mAb-6 | (very wide) | mAb-6 | ~5.621e+013 |
| isotype control | 0.9878 | isotype control | 458.1-1079 | isotype control | 32619 |

As shown in panel 3A and Table 4, all the fitting parameters R2 reached above 0.95; the $EC_{50}$ value of the reference antibody HA22 mAb was 152 ng/mL, and the maximum fluorescence signal of the antibody was between 7506 and 8131 and had entered a plateau phase. The maximum fluorescence signal of mAb-1 was comparable to that of the reference antibody HA22 mAb, while the maximum fluorescence signals of the remaining mAbs were all higher than that of the reference antibody HA22 mAb, and the maximum fluorescence signals can be ranked as: mAb-6>mAb-5>mAb-3>mAb-4>mAb-2>mAb-1>HA22 mAb. Higher fluorescence intensity indicates that the humanized mAbs have higher binding potential on Raji cells than HA22 mAb. At a concentration of 10 ng/ml, a fluorescence signal already could be detected, indicating that binding of each antibody to Raji cells was achieved at 10 ng/mL. Antibodies mAb-3, mAb-5, and mAb-6 still did not reach a fluorescence signal plateau at 50 μg/mL, thereby resulting in inaccurate $EC_{50}$ values, but from the overall linearity evaluation, it can be determined that mAb-1 through mAb-6 had comparable or even stronger binding capacity to Raji cells.

TABLE 6-2

Detection results of binding of the antibodies to CD22 on the cell membrane of REH cells by FACS

| | R2 | | Top | | $EC_{50}$ (ng/mL) |
|---|---|---|---|---|---|
| HA22 mAb | 0.9707 | HA22 mAb | 2364-2868 | HA22 mAb | 172.3 |
| mAb-1 | 0.9520 | mAb-1 | 1847-6579 | mAb-1 | 811.9 |
| mAb-2 | 0.9471 | mAb-2 | (very wide) | mAb-2 | ~3.944e+025 |
| mAb-3 | 0.9494 | mAb-3 | (very wide) | mAb-3 | ~2.2033+012 |
| mAb-4 | 0.9472 | mAb-4 | (very wide) | mAb-4 | ~5.759e+013 |
| mAb-5 | 0.9855 | mAb-5 | (very wide) | mAb-5 | ~4.166e+010 |
| mAb-6 | 0.9709 | mAb-6 | (very wide) | mAb-6 | ~1.114e+099 |
| isotype control | 0.9250 | isotype control | (very wide) | isotype control | ~8.250e+006 |

As shown in panel 3B and Table 6-2, on REH cells with moderate expression of CD22, mAb-1 through mAb-6 had comparable or even stronger binding capacity to REH cells compared to HA22 mAb.

TABLE 6-3

| Detection results of binding of the antibodies to CD22 on the cell membrane of CA46 cells by FACS | | | | | |
|---|---|---|---|---|---|
| | R2 | | Top | | $EC_{50}$ (ng/mL) |
| HA22 mAb | 0.9935 | HA22 mAb | 5724-6118 | HA22 mAb | 221.4 |
| mAb-1 | 0.9866 | mAb-1 | 6789-8271 | mAb-1 | 520.9 |
| mAb-2 | 0.9872 | mAb-2 | 5247-5846 | mAb-2 | 229.7 |
| mAb-3 | 0.9551 | mAb-3 | 2309-17864 | mAb-3 | 1611 |
| mAb-4 | 0.9804 | mAb-4 | 5170-5899 | mAb-4 | 152.5 |
| mAb-5 | 0.9662 | mAb-5 | (very wide) | mAb-5 | ~2.015e+007 |
| mAb-6 | 0.9622 | mAb-6 | 3087-20780 | mAb-6 | 2752 |
| isotype control | 0.8198 | isotype control | (very wide) | isotype control | ~4.590e+006 |

As shown in panel 3C and Table 6-3, on CA46 cells with high expression of CD22, mAb-1 through mAb-6 retained similar binding properties to that of HA22 mAb, all of which achieved high CA46 binding. According to the results of detection on all the three CD22 positive cell lines, humanized mAb-1 to mAb-6 can retain cell binding capacity comparable to or even superior to that of HA22 mAb.

Example 5 Study on Internalization Efficiency of the Antibodies

CD22 is an efficient target for internalization, so the internalization efficiency of an antibody against CD22 is often the most important index of evaluation for the development of immunotoxins and ADCs. To evaluate the internalization efficiency of the humanized antibodies i.e. mAb-1 to mAb-6, three CD22 positive cell lines (Raji, CA46 and REH cells) were selected for the evaluation and the internalization efficiency of the antibodies was compared with that of the reference antibody HA22 mAb.

Reagents:

FACS Buffer: 2% FBS+PBS;

Goat anti-Human IgG (H+L) Secondary Antibody, FITC: Invitrogen, Catalogue number 31529;

4% PFA;

Allophycayanin (APC) AffiniPure $F(ab')_2$ Fragment Goat Anti-Human IgG, Fcγ fragment specific, Jackson Immunoresearch, Catalogue number: 109-136-170.

Experimental steps were as follows:

1) Raji, CA46 and REH cells in logarithmic growth phase were harvested, and centrifuged at 1,000 rpm for 3 min.

2) The cells were washed twice with FACS Buffer, by centrifugation at 1,000 rpm for 3 min.

3) The cells were resuspended in FACS Buffer, and the cell density was adjusted to 5E6/mL.

4) The cell suspensions were added into 96 well round-bottom plates, at 100 μL per well, which were then placed on ice.

5) 100 μg/mL stock solution of an antibody to be tested was prepared, and the solution was added to the wells of the plates, at 100 μL per well, to obtain an antibody concentration of 50 μg/mL; the cells in the plates and the solution were mixed, and then the plates were placed on ice in a 4° C. refrigerator and incubated for 30 min.

6) After the incubation, the plates were taken out and the cells were centrifuged at 2,000 rpm at 4° C. for 3 min.

7) The cells were washed twice with FACS Buffer, by centrifugation at 2,000 rpm at 4° C. for 3 min.

8) One plate was used as the "0 h plate": the cells therein were fixed with 2% PFA for 20 min at room temperature, and then were washed twice with FACS Buffer (2,000 rpm, 3 min), suspended in FACS Buffer, and placed at 4° C. for subsequent secondary antibody labeling.

9) Other plates were used as the "0.5 h plate", the "1 h plate", the "2 h plate", and the "4 h plate": the cells in each well of the plates were suspended in 100 μL of FACS Buffer, and the plates were placed at a 37° C. constant temperature incubator for stationary culture and the culture time was recorded.

10) The plates were taken out at 0.5 h, 1 h, 2 h and 4 h respectively.

11) All the plates were centrifuged at 2,000 rpm at 4° C. for 3 min.

12) The secondary antibodies were formulated in buffers; and 100 μL of each were added into the cells and the plates were then placed on ice in a 4° C. refrigerator and incubated for 30 min.

13) After the incubation, the cells were centrifuged at 2,000 rpm 4° C. for 3 min.

14) Supernatants were discarded, and the cells were washed twice with FACS Buffer by centrifugation at 2,000 rpm 4° C. for 3 min.

15) The cells were suspended in 200 μL of FACS Buffer, and were detected.

Figure 4:
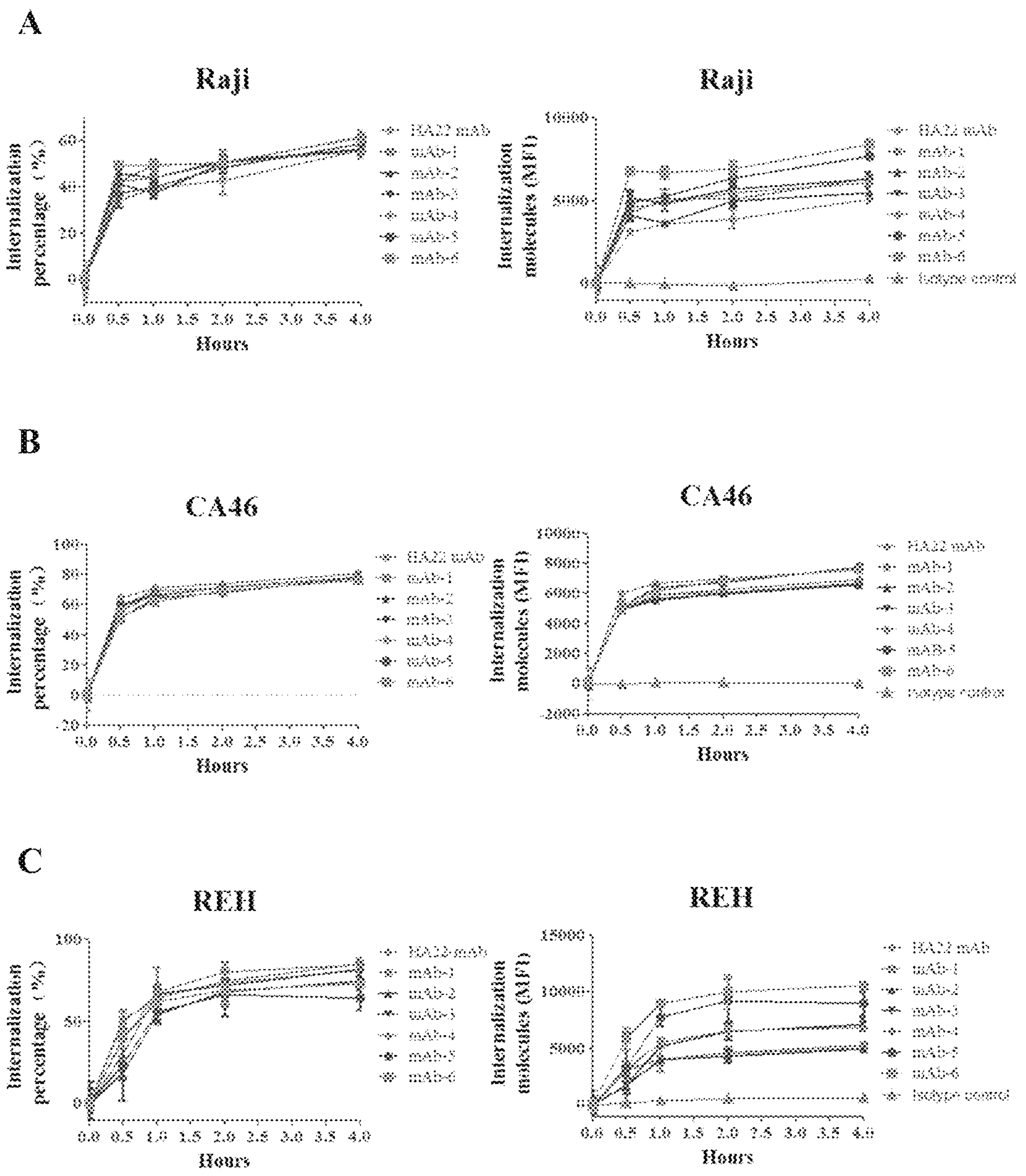
FIG. 4 shows detection results of endocytosis of the antibodies provided by the present disclosure by flow cytometry (FACS), in which panel 4A: Raji cells; panel 4B: CA46 cells; and panel 4C: REH cells.

Results are shown in FIG. 4.

At 0 h, no endocytosis occurred, the antibodies were 100% concentrated on the cell surface; and the antibodies were endocytosed into the cells over time and the amounts of the antibodies on the membrane surface which could be detected decreased. The lower antibody signal is detected, the more endocytosis occurs. As shown in FIG. 4, no significant difference in the endocytosis rates was found between mAb-1 to mAb-6 and HA22 mAb when endocytosis percentages of the antibodies into the Raji, CA46 and REH cells were evaluated, with maximal endocytosis efficiency achieved at 0.5 h on Raji and CA46 cells and at 1 h on REH cells. Although the 7 antibodies showed comparable endocytosis percentages, a large difference in the number of endocytosed molecules could be found by analysis of the mean fluorescence intensity values. On the CA46 cells, the antibodies achieved essentially identical number of endocytosed molecules, while on the Raji and REH cells, the numbers of endocytosed molecules of the humanized antibodies mAb-1 to mAb-6 were significantly higher than that of the reference antibody HA22 mAb, and could be ranked from high to low as follows: mAb-6>mAb-5>mAb-4>mAb-3>mAb-2=mAb-1=HA22 mAb.

Example 6 Detection of Antibody-Dependent Cell-Mediated Cytotoxicity (ADCC) of the Antibodies To evaluate whether the candidate antibodies have antibody-dependent cell-mediated cytotoxicity, three tumor cell lines, i.e., Raji, CA46 and REH cell lines having different CD22 expression levels were selected as target cells and PBMC as effector cells for ADCC assay.

Reagent:

R-10 medium: phenol red-free RPMI 1640+10% inactivated FBS+2 mM Glutamax;

R-2 medium: phenol red-free RPMI 1640+2% inactivated FBS+2 mM Glutamax;

Cytotox Glo™ Cytotoxity Assay kit (Promega, Catalog number: G9291).

Experimental steps were as follows:

1) PBMCs were thawed one day in advance.

2) On the day of the experiment, the thawed PBMCs were harvested, centrifuged at 200 g for 15 min, and the supernatant was discarded. The cells were resuspended in 2 mL of fresh R-10 medium, counted, and the cell density was adjusted to 5E6 cells/mL. The cell suspension was added into plates, at 50 μL per well to obtain 250000 cells per well, or R-10 medium was added.

3) An antibody to be detected was diluted to 200 μg/mL, 40 μg/mL, 8 μg/mL, 1.6 μg/mL, 0.32 μg/mL, 0.064 μg/mL, 0.0128 μg/mL, and 0.00256 μg/mL with R-2 medium, and added into the plates, at 25 μL per well to obtain final concentrations of 50 μg/mL, 10 μg/mL, 2 μg/mL, 0.4 μg/mL, 0.08 μg/mL, 0.016 μg/mL, 0.0032 μg/mL, and 0.00064 μg/mL.

4) The Raji, CA46 and REH cells were diluted to 2E5 cells/mL with R-10 medium, and added into the plates, at 25 μL per well, to achieve an effector-to-target ratio of 50:1.

5) The plates were incubated at 37° C., 5% $CO_2$ for 4 h, and the color developed and was detected according to the instructions in the Cytotox Glo™ Cytotoxity Assay kit.

Figure 5:
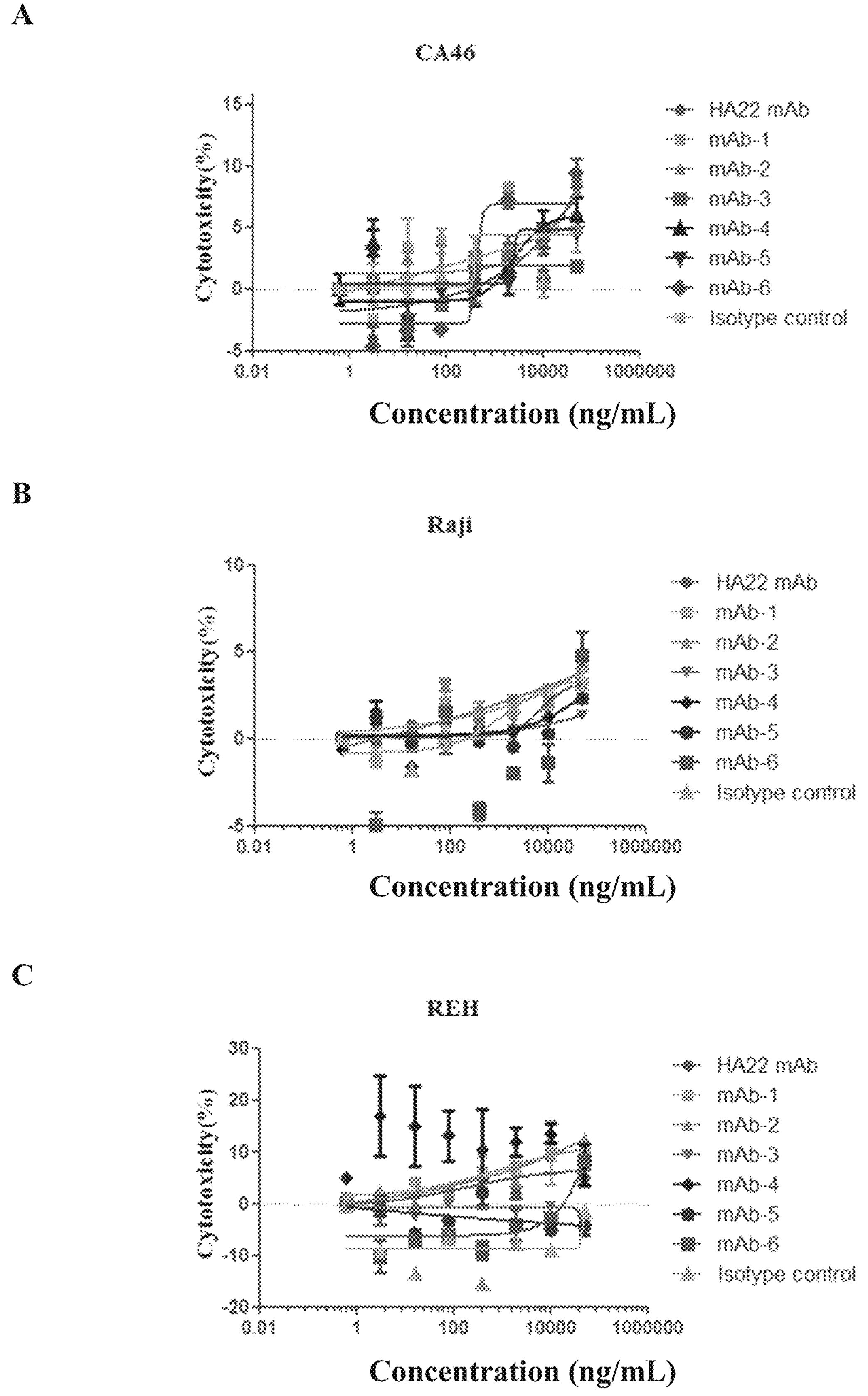
FIG. 5 shows detection results of ADCC activity of the antibodies provided by the present disclosure, in which panel 5A: CA46 cells; panel 5B: Raji cells; and panel 5C: REH cells.
Figure 6:
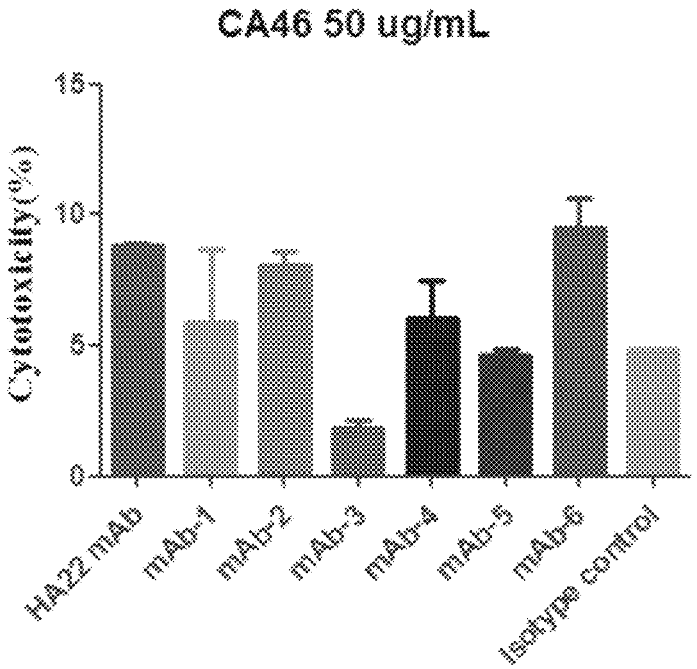
FIG. 6 shows detection results of ADCC activity of the antibodies provided by the present disclosure at a high dose of 50 μg/mL, in which panel 6A: CA46 cells; panel 6B: Raji cells; and panel 6C: REH cells.
Figure 6:
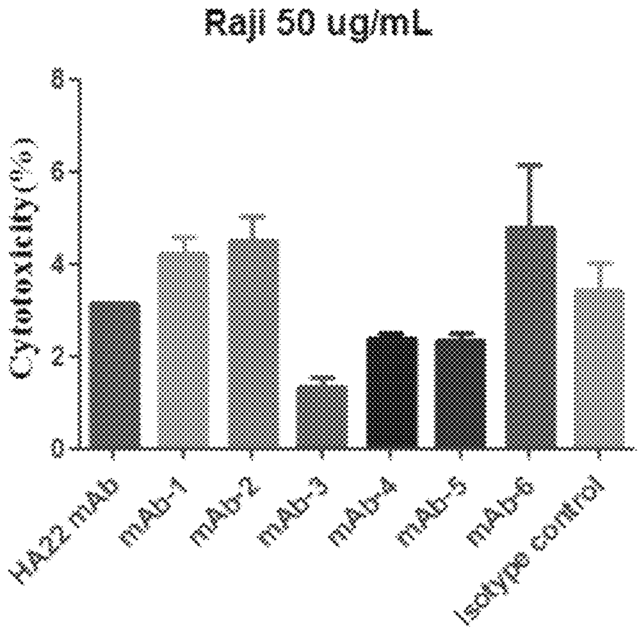
Figure 6:
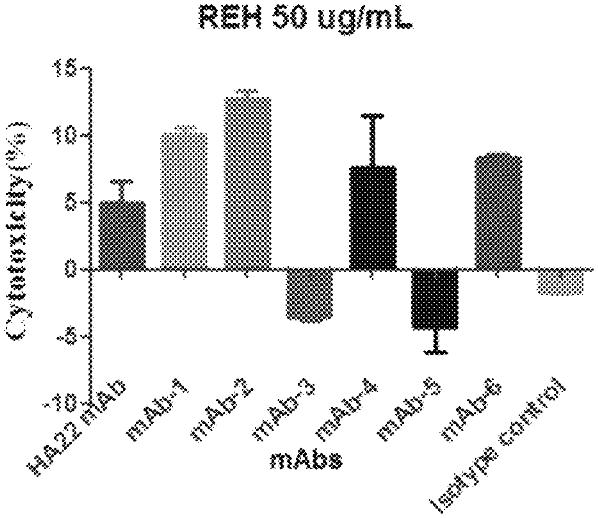

Results are shown in FIGS. 5 and 6.

As shown in FIG. 5, all the 7 mabs had no significant ADCC effects on the tumor cells with different CD22 expression levels, and a dose-response dependence curve could not be fitted; while they exhibited slight ADCC effects at the high dose of 50 μg/mL.

The cytotoxicities observed at the dose of 50 μg/mL were analyzed, and as shown in FIG. 6, mAb-3 showed a relatively low cytotoxicity, having no difference from an isotype control. Antibodies mAb-1, mAb-2, mAb-4, mAb-5, and mAb-6 showed no different cytotoxicities from HA22 on the Raji and CA46 cells having high CD22 expression levels. However, mAb-2 showed a slightly more potent cytotoxicity than HA22 mAb on REH cells having a lower CD22 expression level. In conclusion, no significant ADCC effect was shown by the 7 IgG1 antibodies.

The above description of the embodiments of the present invention is not intended to limit the present invention, and those skilled in the art may make various changes and modifications to the present invention without departing from the spirit of the present invention, which should fall within the scope of the appended claims.

What is claimed is:

1. An isolated anti-CD22 antibody or antigen-binding fragment thereof, comprising a heavy chain variable region (VH) and a light chain variable region (VL), wherein the heavy chain variable region (VH) and the light chain variable region (VL) comprise respectively:

(1) H-CDR1 having the amino acid sequence shown in SEQ ID NO: 19, H-CDR2 having the amino acid sequence shown in SEQ ID NO: 25, and H-CDR3 having the amino acid sequence shown in SEQ ID NO: 21; and, L-CDR1 having the amino acid sequence shown in SEQ ID NO: 22, L-CDR2 having the amino acid sequence shown in SEQ ID NO: 23, and L-CDR3 having the amino acid sequence shown in SEQ ID NO: 24; or (2) H-CDR1 having the amino acid sequence shown in SEQ ID NO: 19, H-CDR2 having the amino acid sequence shown in SEQ ID NO: 26, and H-CDR3 having the amino acid sequence as shown in SEQ ID NO: 21; and, L-CDR1 having the amino acid sequence shown in SEQ ID NO: 22, L-CDR2 having the amino acid sequence shown in SEQ ID NO: 23, and L-CDR3 having the amino acid sequence shown in SEQ ID NO: 24.

2. The antibody or antigen-binding fragment thereof according to claim 1, wherein the heavy chain variable region comprises the amino acid sequence shown in SEQ ID NO: 4, SEQ ID NO: 3, SEQ ID NO: 6, or SEQ ID NO: 5; and, the light chain variable region comprises the amino acid sequence shown in SEQ ID NO: 2, SEQ ID NO: 7, or SEQ ID NO: 8.

3. The antibody or antigen-binding fragment thereof according to claim 1, wherein the heavy chain variable region and the light chain variable region comprise respectively:

(1) the amino acid sequence shown in SEQ ID NO: 4; and, the amino acid sequence shown in SEQ ID NO: 2;

(2) the amino acid sequence shown in SEQ ID NO: 4; and, the amino acid sequence shown in SEQ ID NO: 7;

(3) the amino acid sequence shown in SEQ ID NO: 3; and, the amino acid sequence as shown in SEQ ID NO: 7;

(4) the amino acid sequence shown in SEQ ID NO: 3; and, the amino acid sequence shown in SEQ ID NO: 8;

(5) the amino acid sequence shown in SEQ ID NO: 6; and, the amino acid sequence shown in SEQ ID NO: 8; or (6) the amino acid sequence shown in SEQ ID NO: 5; and, the amino acid sequence shown in SEQ ID NO: 8.

4. The antibody or antigen-binding fragment thereof according to claim 1, wherein the antibody is a murine antibody, a chimeric antibody or a fully or partially humanized antibody; or the antibody is in the form of a scFv, dsFv, $(dsFv)_2$, Fab, Fab', $F(ab')_2$ or Fv antibody.

5. The antibody or antigen-binding fragment thereof according to claim 1, wherein the antibody is a monoclonal antibody.

6. An isolated nucleic acid molecule comprising a nucleotide sequence encoding the anti-CD22 antibody or antigen-binding fragment thereof according to claim 1.

7. An isolated vector comprising the nucleic acid molecule according to claim 6.

8. An isolated host cell comprising the nucleic acid molecule according to claim 6 or an isolated vector comprising the nucleic acid molecule, or transformed or transfected with the nucleic acid molecule and/or the vector.

9. A composition comprising the antibody or antigen-binding fragment thereof according to claim 1 and a pharmaceutically acceptable carrier, adjuvant, or excipient.

10. An immunoconjugate comprising the antibody or antigen-binding fragment thereof according to claim 1 and a partner molecule which is a therapeutic agent.

11. A kit comprising the antibody or antigen-binding fragment thereof according to claim 1.

12. A method for treating a CD22-expressing disease, the method comprising administering to a subject in need thereof the antibody or antigen-binding fragment thereof according to claim 1.

13. The antibody or antigen-binding fragment thereof according to claim 1, wherein the antibody further comprises a human or murine heavy chain constant region and/or light chain constant region.

14. The antibody or antigen-binding fragment thereof according to claim 1, wherein the antibody comprises a heavy chain constant region selected from the group consisting of IgG, IgA, IgM, IgD and IgE and/or a kappa or lambda type light chain constant region.

15. The antibody or antigen-binding fragment thereof according to claim 5, wherein the monoclonal antibody comprises a light chain which is of a kappa type.

16. The antibody or antigen-binding fragment thereof according to claim 5, wherein the monoclonal antibody is an IgG1 antibody.

17. The method according to claim 12, wherein the disease is a tumor or cancer expressing CD22.

18. The method according to claim 12, wherein the disease is a CD22-related B cell malignant tumor.

19. The method according to claim 12, wherein the disease is CD22 high expressing lymphoma or leukemia.

20. The method according to claim 19, wherein the lymphoma is Non-Hodgkin's lymphoma, small lymphocytic lymphoma or mantle cell lymphoma; and the leukemia is chronic lymphocytic leukemia, hairy cell leukemia or acute lymphocytic leukemia.

* * * * *